(12) United States Patent
Parvulescu et al.

(10) Patent No.: US 9,371,239 B2
(45) Date of Patent: *Jun. 21, 2016

(54) TIN-CONTAINING ZEOLITIC MATERIAL HAVING AN MWW-TYPE FRAMEWORK STRUCTURE

(71) Applicant: BASF SE, Ludwigshafen (DE)

(72) Inventors: Andrei-Nicolae Parvulescu, Heidelberg (DE); Ulrich Müller, Neustadt (DE); Joaquim Henrique Teles, Waldsee (DE); Nicolas Vautravers, Mannheim (DE); Bernd Hinrichsen, Stuttgart (DE); Gerhard Cox, Bad Dürkheim (DE); Richard Jacubinas, Bloomfield, NJ (US)

(73) Assignee: BASF SE, Ludwigshafen (DE)

( * ) Notice: Subject to any disclaimer, the term of this patent is extended or adjusted under 35 U.S.C. 154(b) by 226 days.

This patent is subject to a terminal disclaimer.

(21) Appl. No.: 14/072,286

(22) Filed: Nov. 5, 2013

(65) Prior Publication Data

US 2014/0163243 A1 Jun. 12, 2014

Related U.S. Application Data

(60) Provisional application No. 61/722,276, filed on Nov. 5, 2012.

(51) Int. Cl.

| | | |
|---|---|---|
| *C01B 39/00* | (2006.01) | |
| *B01J 37/10* | (2006.01) | |
| *B01J 29/70* | (2006.01) | |
| *C01B 39/02* | (2006.01) | |
| *C01B 39/06* | (2006.01) | |
| *C01B 39/48* | (2006.01) | |
| *C01B 39/12* | (2006.01) | |
| *C07D 313/04* | (2006.01) | |
| *B01J 29/86* | (2006.01) | |

(52) U.S. Cl.
CPC ........... *C01B 39/026* (2013.01); *B01J 29/7088* (2013.01); *B01J 37/10* (2013.01); *C01B 39/06* (2013.01); *C01B 39/12* (2013.01); *C01B 39/48* (2013.01); *B01J 29/86* (2013.01); *B01J 2229/183* (2013.01); *B01J 2229/37* (2013.01); *B01J 2229/40* (2013.01); *B01J 2229/42* (2013.01); *C07D 313/04* (2013.01)

(58) Field of Classification Search
CPC ...... C01B 39/026; C01B 39/12; C01B 39/06; B01J 29/7088; B01J 29/86; B01J 2229/183; C07D 313/04

See application file for complete search history.

(56) References Cited

U.S. PATENT DOCUMENTS

| | | | |
|---|---|---|---|
| 5,968,473 A | 10/1999 | Valencia et al. | |
| 6,306,364 B1 | 10/2001 | Valencia et al. | |
| 7,326,401 B2 | 2/2008 | Tatsumi et al. | |

FOREIGN PATENT DOCUMENTS

| | | | |
|---|---|---|---|
| WO | WO-03/074422 A1 | | 9/2003 |
| WO | WO 2013/117537 A1 | | 8/2013 |
| WO | WO2013117537 | * | 8/2013 |

OTHER PUBLICATIONS

International Search Report and Written Opinion for PCT/EP2013/073020 dated Apr. 9, 2014.
Hammond et al., "Simple and Scalable Preparation of Highly Active Lewis Acidic Sn-β*", Angewandte Chemie International Edition, vol. 51, Issue 47, pp. 11736-11739, Nov. 19, 2012.
Liu, Guanqi, et al., "Hydrothermal Synthesis of MWW-Type Stannosilicate and its Post-Structural Transformation to MCM-56 Analogue", Microporous and Mesoporous Materials, vol. 165, (2013), pp. 210-218.
Corma, Avelino, et al., "Sn-Zeolite Beta as a Heterogeneous Chemoselective Catalyst for Baeyer-Villiger Oxidations", Nature, vol. 412, (2001), pp. 423-425.
Corma, Avelino, et al., "A New, Alternative, Halogen-Free Synthesis for the Fragrance Compound Melonal Using Zeolites and Mesoporous Materials as Oxidation Catalysts", Journal of Catalysis, vol. 234, (2005), pp. 96-100.

* cited by examiner

*Primary Examiner* — David M Brunsman
(74) *Attorney, Agent, or Firm* — Drinker Biddle & Reath LLP

(57) ABSTRACT

A tin containing zeolitic material having an MWW-type framework structure (Sn-MWW), having a tin content of at most 2 weight-%, calculated as element and based on the weight of the Sn-MWW, and having an X-ray diffraction pattern comprising peaks at 2 theta diffraction angles of (6.6±0.1)°, (7.1±0.1)°, and (7.9±0.1)°.

34 Claims, 4 Drawing Sheets

TIN-CONTAINING ZEOLITIC MATERIAL HAVING AN MWW-TYPE FRAMEWORK STRUCTURE

CROSS-REFERENCE TO RELATED APPLICATIONS

Figure 1:
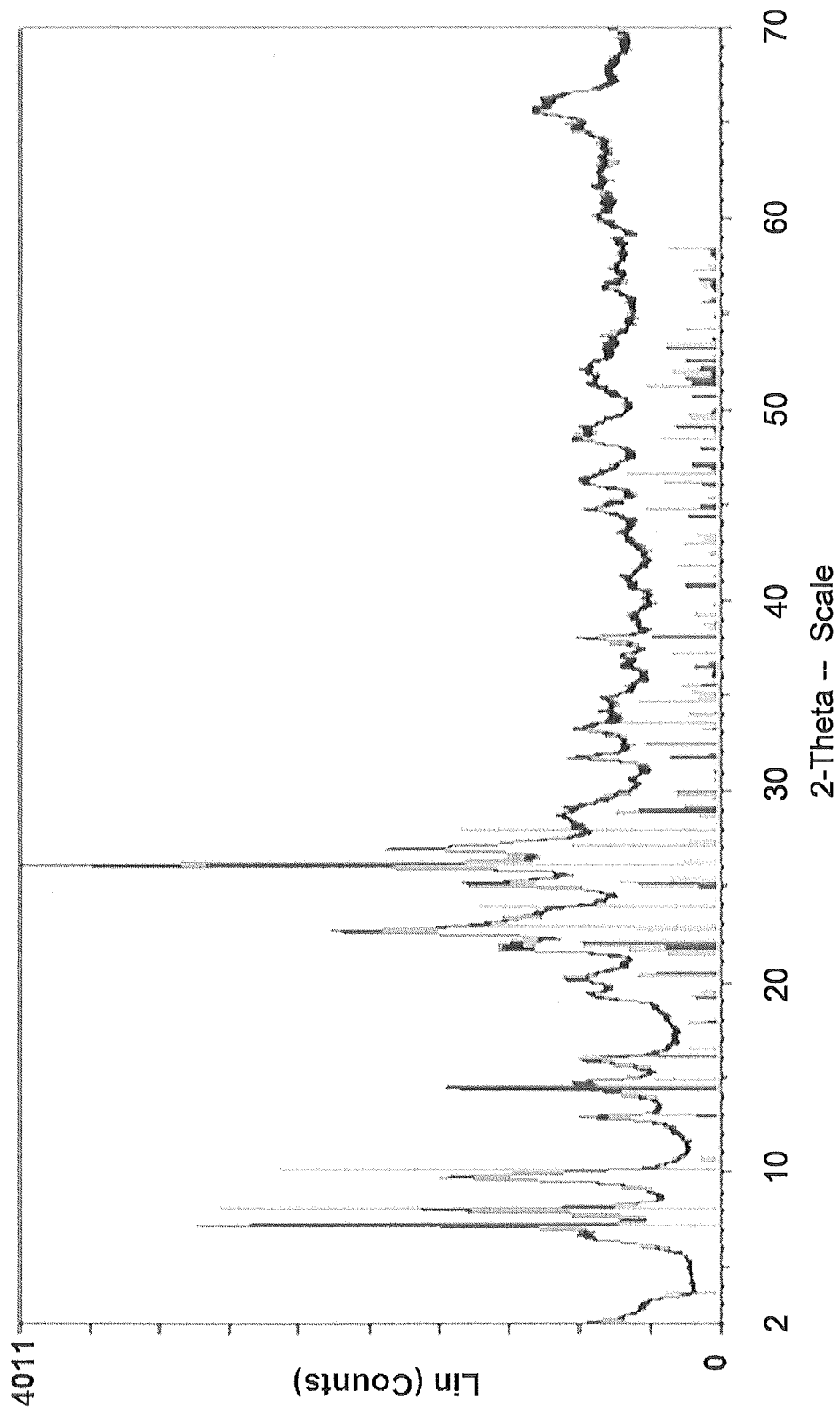

This application claims benefit (under 35 USC 119(e)) of U.S. Provisional Application No. 61/722,276, filed Nov. 5, 2012, which is incorporated by reference.

The present invention relates to a novel tin-containing zeolitic material having an MWW-type framework structure and a preferred process for its preparation. Further, the present invention relates to preferred uses of this novel tin-containing zeolitic material having an MWW-type framework structure.

Zeolites are widely used in the chemical industry, for example as heterogeneous catalysts for various chemical and petrochemical processes. Therefore, providing zeolitic materials with novel framework topologies plays a crucial role in the development of catalysts, catalyst components, and catalyst support materials. For certain applications, it is advantageous that the zeolitic materials, in addition to Si and/or Al, may contain at least one further heteroatom.

In Nature 412 (2001), pages 423-425, and in Journal of Catalysis 234 (2005), pages 96-100, a tin-containing zeolite Beta is described for the use in the Baeyer-Villiger reaction. However, tin-containing zeolite Beta materials are comparatively difficult to prepare which renders this prior art process disadvantageous since the synthesis of the catalyst, disclosed in U.S. Pat. No. 5,968,473 and U.S. Pat. No. 6,306,364, is technically difficult to scale-up due to low yield, high synthesis times of more than 15 days, the use of HF and chlorinated Sn precursor compounds.

WO 03/074422 A1 and U.S. Pat. No. 7,326,401 B2 describe a process for synthesizing a zeolite material having MWW structure. A tin-containing MWW is mentioned in the description, having a very high tin loading of about 4.7 weight-%. This tin-containing MWW is prepared from a boron-containing (B-MWW) zeolite precursor which is deboronated by acid treatment before the Sn is introduced.

Furthermore, in Microporous and Mesoporous Materials 165 (2013), pages 210-218, the use of a tin-containing zeolitic material having an MWW framework structure in the Baeyer-Villiger reaction of 2-adamantanone is described. According to this document, the zeolitic materials are obtained from a boron-containing precursor material which is not subjected to deboronation resulting in a material having a comparatively high boron content.

Surprisingly, it was found that by introducing a specific amount of tin into a specifically deboronated MWW zeolite leads to a novel tin-containing zeolitic material having an MWW-type framework structure. Further, it was found that this novel material exhibits advantageous characteristics, in particular if used as a catalytically active material, more specifically as a catalytically active material in Baeyer-Villiger oxidation-type reactions.

In particular, it was found that a combination of a deboronation of a boron-containing zeolitic material having an MWW framework structure with a liquid solvent system having a pH in the range of from 5.5 to 8 and the incorporation of a specific amount of tin in the such deboronated material via hydrothermal treatment, followed by a specific acidic treatment, leads to this novel zeolitic material having an MWW-type framework structure which, compared to the prior art materials, has a higher interlayer distance characterized by the c parameter as determined via XRD.

Therefore, the present invention relates to a process for preparing a tin-containing zeolitic material having an MWW-type framework structure (Sn-MWW) comprising (i) providing a boron-containing zeolitic material having an MWW framework structure comprising $SiO_2$ and $B_2O_3$ (B-MWW);

(ii) deboronating the B-MWW by treating the B-MWW provided in (i) with a liquid solvent system having a pH in the range of from 5.5 to 8;

(iii) incorporating Sn into the deboronated B-MWW obtained from (ii) by a process comprising (iii.1) preparing an aqueous synthesis mixture containing the deboronated B-MWW obtained from (ii), an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a tin source, wherein in the synthesis mixture, the molar ratio of Sn, calculated as $SnO_2$, relative to Si, calculated as $SiO_2$ and contained in the deboronated B-MWW, is at most 0.015:1;

(iii.2) hydrothermally synthesizing a tin-containing zeolitic material having an MWW-type framework structure from the synthesis mixture obtained from (iii.1) thereby obtaining a tin-containing zeolitic material having an MWW-type framework structure in its mother liquor;

(iii.3) separating the tin-containing zeolitic material having an MWW-type framework structure obtained from (iii.2) from its mother liquor;

(iv) treating the tin-containing zeolitic material having an MWW-type framework structure obtained from (iii) with an aqueous solution having a pH of at most 5 thereby obtaining the Sn-MWW having an Sn content of at most 2 weight-%, calculated as element and based on the weight of the Sn-MWW, and optionally separating the Sn-MWW from the aqueous solution.

Also, the present invention relates to a tin containing zeolitic material having an MWW-type framework structure (Sn-MWW), having a tin content of at most 2 weight-%, calculated as element and based on the weight of the Sn-MWW, and having an X-ray diffraction pattern comprising a peak at a 2 theta diffraction angle of $(6.6\pm0.1)°$, preferably a peak at a 2 theta diffraction angle of $(6.6\pm0.1)°$, a peak at a 2 theta diffraction angle of $(7.1\pm0.1)°$, and a peak at a 2 theta diffraction angle of $(7.9\pm0.1)°$.

Step (i)

Generally, there are no specific restrictions how the B-MWW is provided in (i). For example, it may be conceivable to purchase a suitable, commercially available boron-containing zeolitic material having an MWW framework structure. Further, for example, any conceivable process for synthesizing such a zeolite can be employed for providing the zeolitic material. Preferably, the zeolitic material is provided in (i) by a process including hydrothermally synthesizing the zeolitic material starting from suitable sources of $B_2O_3$ and $SiO_2$ in the presence of a suitable template compound, also referred to as structure directing agent.

Preferably, the B-MWW is provided in (i) by a process comprising (a) hydrothermally synthesizing a B-MWW precursor from an aqueous synthesis mixture containing a silicon source, preferably ammonia stabilized colloidal silica, a boron source, preferably boric acid, and an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyl-trimethylammonium hydroxide, and a mixture of two or more thereof, to obtain the B-MWW precursor in its mother liquor;

(b) separating the B-MWW precursor from its mother liquor, preferably comprising drying the B-MWW precursor, wherein the drying is preferably carried out at a temperature in the range of from 100 to 180° C., more preferably from 110 to 140° C., wherein in the synthesis mixture in (a), the molar ratio of B, calculated as $B_2O_3$ and contained in the boron source, relative to Si, calculated as $SiO_2$ and contained in the Si source, is preferably in the range of from 0.4:1 to 0.6:1, more preferably from 0.45:1 to 0.55:1, more preferably from 0.47:1 to 0.52:1;

the molar ratio of the MWW template compound, relative to Si, calculated as $SiO_2$ and contained in the Si source, is preferably in the range of from 0.8:1 to 1.7:1, more preferably from 1.0:1 to 1.5:1, more preferably from 1.1:1 to 1.3:1; and the molar ratio of $H_2O$ relative to Si, calculated as $SiO_2$ and contained in the Si source, is preferably in the range of from 12:1 to 20:1, more preferably from 13:1 to 18:1, more preferably from 14:1 to 16:1.

As far as the silicon source used in (a) is concerned, no specific restrictions exist. Preferably, the silicon source is a fumed silica or a colloidal silica such as ammonia-stabilized colloidal silica, with ammonia-stabilized colloidal silica being especially preferred.

As far as the boron source used in (a) is concerned, no specific restrictions exist. Preferably, the boron source is boric acid, a borate, in particular a water-soluble borate, a boron halide, boron oxide ($B_2O_3$), with boric acid being especially preferred.

As far as the amounts of silicon source and boron source in (a) are concerned, no specific restrictions exist provided that the B-MWW precursor is obtained. Preferably, the molar ratio of B, calculated as $B_2O_3$ and contained in the boron source, relative to Si, calculated as $SiO_2$ and contained in the Si source, is at least 0.4:1, more preferably in the range of from 0.4:1 to 1:1, more preferably from 0.4:1 to 0.8:1, more preferably from 0.4:1 to 0.6:1, more preferably from 0.45:1 to 0.55:1, more preferably from 0.47:1 to 0.52:1.

As far as the MWW template compound in (a) is concerned, no specific restrictions exist provided that the B-MWW precursor is obtained. Preferably, the MWW template compound is selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof. More preferably, the MWW template compound is piperidine.

As far as the amounts of silicon source and MWW template compound in (a) are concerned, no specific restrictions exist provided that the B-MWW precursor is obtained. Preferably, in (a), the molar ratio of the MWW template compound, relative to Si, calculated as $SiO_2$ and contained in the Si source, is in the range of from 0.8:1 to 1.7:1, more preferably from 1.0:1 to 1.5:1, more preferably from 1.1:1 to 1.3:1.

As far as the amounts of silicon source and water in (a) are concerned, no specific restrictions exist provided that the B-MWW precursor is obtained. Preferably, in (a), the molar ratio of $H_2O$ relative to Si, calculated as $SiO_2$ and contained in the Si source, is in the range of from 12:1 to 20:1, more preferably from 13:1 to 18:1, more preferably from 14:1 to 16:1.

According to (a), the aqueous synthesis mixture is preferably subjected to a hydrothermal synthesis under autogenous pressure, wherein the B-MWW precursor is crystallized during the hydrothermal synthesis. For crystallization purposes, it is conceivable to use at least one suitable seeding material such as a zeolitic material having MWW framework structure. Preferably, the crystallization time is in the range of from 3 to 8 days, more preferably from 4 to 6 days. During hydrothermal synthesis, the crystallization mixture may be stirred. The stirring rates can be suitably chosen depending, for example, on the volume of the aqueous synthesis mixture, the amount of the starting materials employed, the desired temperature, and the like. For example, the stirring rate is in the range of from 50 to 300 r.p.m. (rounds per minute), such as from 70 to 250 r.p.m. or from 90 to 120 r.p.m.

The temperature applied during the hydrothermal synthesis is preferably in the range of from 160 to 200° C., more preferably from 160° C. to 190° C., more preferably from 160 to 180° C.

After hydrothermal synthesis, the obtained B-MWW precursor is preferably suitably separated from its mother liquor according to (b). All conceivable methods of separating a B-MWW precursor from its mother liquor are possible. These methods include, for example, filtration, ultrafiltration, diafiltration and centrifugation methods or, for instance, spray drying processes and spray granulation processes. A combination of two or more of these methods can be applied.

Preferably, the B-MWW precursor is separated from its mother liquid by filtration, and the thus obtained material, for example in the form of a filter cake, is preferably subjected to washing with at least one suitable washing agent, preferably to washing with water, at a temperature of up to 50° C., preferably from 15 to 50° C., more preferably from 15 to 35° C., more preferably from 20 to 30° C. Subsequently, the filter cake is preferably suspended in a suitable liquid, preferably water, to allow the preferred spray-drying or to ultrafiltration. The solids content of such suspension can be suitably chosen to meet the requirements of the preferred spray-drying or to ultrafiltration. It is also conceivable to separate the B-MWW precursor directly from its mother liquor by spray-drying or spray-granulation, preferably spray-drying. In this case, it is possible to suitably increase the B-MWW precursor content of the mother liquor prior to separation by concentrating the suspension. Concentrating may be achieved, for example, by suitable evaporation. If the drying is accomplished by spray-drying, the drying gas inlet temperature is preferably in the range of from 200 to 250° C., more preferably from 220 to 250° C., and the drying gas outlet temperature is preferably in the range of from 100 to 175° C., more preferably from 120 to 150° C.

If washing is applied, it is preferred to continue the washing process until the washing water has a conductivity of at most 1,000 microSiemens/cm, more preferably of at most 800 microSiemens/cm, more preferably of at most 500 microSiemens/cm.

After separation of the B-MWW precursor from the suspension, preferably by filtration, and preferably after washing, the washed B-MWW precursor is optionally subjected to pre-drying, for example by subjecting to a suitable gas stream such as air, lean air, or technical nitrogen, for a time preferably in the range of from 4 to 10 h, more preferably from 5 to 8 h. Subsequently, the optionally pre-dried filter cake is preferably dried, either by the preferred spray-drying as described above or by conventional drying. Preferably, drying is carried out in a suitable atmosphere such as technical nitrogen, air, or lean air. The conventional drying can be accomplished, for example, in a suitable drying oven, preferably carried out for a period in the range of from 1 to 10 h, more preferably from 2 to 6 h.

After the preferred drying, the B-MWW precursor is subjected to calcination to obtain the B-MWW zeolitic material. During calcination, the MWW template compound is preferably at least partially, more preferably essentially completely removed from the framework structure. Preferred calcination temperatures are the range of from 400 to 700° C., more preferably from 500 to 675° C., more preferably from 550 to 650° C. Preferred atmosphere under which the calcination is carried out include technical nitrogen, air, or lean air. Preferred calcination times are in the range of from 0.5 to 12 h, more preferably from 1 to 10 h, more preferably from 2 to 6 h.

Generally, the framework structure of the zeolitic material provided in (i) comprises $B_2O_3$ and $SiO_2$. Preferably, the suitable sources of $B_2O_3$ and $SiO_2$ as described above are employed in an amount and subjected to hydrothermal synthesis conditions so that at least 95 weight-%, preferably at least 98 weight-%, more preferably at least 99 weight-%, more preferably at least 99.5 weight-% such as at least 99.6 weight-%, at least 99.7 weight-%, at least 99.8 weight-%, or at least 99.9 of the framework structure of the B-MWW provided in (i) consist of $B_2O_3$ and $SiO_2$. In particular, the B-MWW provided in (i) is free of aluminum which, in the context of the present invention, relates to a B-MWW which may contain aluminum only in traces as impurity.

Generally, the molar ratio $B_2O_3:SiO_2$ of the framework structure of the B-MWW provided in (i) is not specifically restricted. Preferably, the molar ratio $B_2O_3:SiO_2$ of the B-MWW is at least 0.03:1, more preferably in the range of from 0.03:1 to 0.1:1, more preferably from 0.03:1 to 0.09:1, more preferably from 0.03:1 to 0.08:1, more preferably from 0.03:1 to 0.07:1. Thus, conceivable preferred molar ratios $B_2O_3:SiO_2$ are in the range of from 0.03:1 to 0.06:1 or from 0.03:1 to 0.05:1 or from 0.03:1 to 0.04:1 or from 0.04:1 to 0.07:1 or from 0.04:1 to 0.06:1 or from 0.04:1 to 0.05:1 or from 0.05:1 to 0.07:1 or from 0.05:1 to 0.06:1 or from 0.06:1 to 0.07:1.

Step (ii)

According to the present invention, the B-MWW, especially preferably the separated, dried, preferably spray-dried, and calcined B-MWW provided in (i), is preferably subjected to deboronation in (ii) by a treatment with a liquid solvent system having a pH in the range of from 5.5 to 8.

Generally, no specific restrictions exist concerning the chemical nature of the liquid solvent system used in (ii). Preferably, the liquid solvent system used in (ii) is selected from the group consisting of water, monohydric alcohols, polyhydric alcohols, and mixtures of two or more thereof. Concerning the monohydric alcohols and polyhydric alcohols, no specific restrictions exist. Preferably, these alcohols contain from 1 to 6 carbon atoms, more preferably from 1 to 5 carbon atoms, more preferably from 1 to 4 carbon atoms, and more preferably from 1 to 3 carbon atoms. The polyhydric alcohols preferably comprise from 2 to 5 hydroxyl groups, more preferably from 2 to 4 hydroxyl groups, preferably 2 or 3 hydroxyl groups. Especially preferred monohydric alcohols are methanol, ethanol, and propanol like 1-propanol and 2-propanol. Especially preferred polyhydric alcohols are ethane-1,2-diol, propane-1,2-diol, propane-1,3-diol, and propane-1,2,3-triol. If mixtures of two or more of the above-described compounds are employed, it is preferred that these mixtures comprise water and at least one monohydric and/or at least one polyhydric alcohol. Most preferably, the liquid solvent system used in (ii) consists of water.

Further, it is especially preferred that the liquid solvent system does not contain an inorganic acid or an organic acid, or a salt thereof, the acid being selected from the group consisting of hydrochloric acid, sulfuric acid, nitric acid, phosphoric acid, formic acid, acetic acid, propionic acid, oxalic acid, and tartaric acid. Therefore, the present invention also relates to the process above, wherein the liquid solvent system is selected from the group consisting of water, methanol, ethanol, propanol, ethane-1,2-diol, propane-1,2-propane-1,3-diol, propane-1,2,3-triol, and mixtures of two or more thereof, preferably water, and wherein the liquid solvent system does not contain an inorganic or organic acid, or a salt thereof, the acid being selected from the group consisting of hydrochloric acid, sulfuric acid, nitric acid, phosphoric acid, formic acid, acetic acid, propionic acid, oxalic acid, and tartaric acid. Even more preferably, in (ii), the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, wherein the liquid solvent system does not contain an inorganic or organic acid, or a salt thereof.

As far as the amount of B-MWW which is employed in (ii) relative to the amount of liquid solvent system is concerned, no specific restrictions exist. Preferably, the weight ratio of the liquid solvent system relative to B-MWW is in the range of from 40:1 to 5:1, more preferably from 30:1 to 7:1, more preferably from 20:1 to 10:1.

The treating conditions according to (ii) are not specifically restricted, provided that the solvent system described above is in its liquid state. In particular, concerning the preferred temperatures described below, the skilled person will choose the respective pressure under which the treating is carried out in order to keep the solvent system in its liquid state. Preferably, in (ii), the treating is carried out at a temperature in the range of from 50 to 125° C., more preferably from 90 to 115° C., more preferably from 95 to 105° C.

Concerning the duration of the treatment according to (ii), no specific restrictions exist. The above mentioned time is to be understood as the time for which the liquid solvent system is maintained under the above-described treating temperature. Preferably, in (ii), the treating is carried out for a period in the range of from 6 to 20 h, more preferably from 7 to 17 h, more preferably from 8 to 12 h.

As to the type of vessel in which the treatment in (ii) is conducted, no particular restrictions exist. Preferably, the vessel is suitably selected to allow to treat the zeolitic material at the temperatures described above, at which temperatures the solvent system is in its liquid state. Therefore, as far as higher temperatures are concerned, in (ii), the treating is carried out in a closed system under autogenous pressure.

Further, according to an alternative preferred embodiment of the present invention, in (ii), the treating is carried out in an open system under reflux. Thus, the preferred vessel, representing an open system, used for the treating according to (ii) is preferably equipped with a reflux condenser.

During the treatment in (ii), the temperature of the liquid solvent system is kept essentially constant or is changed, the treating with the liquid solvent system thus being carried out at two or more different temperatures. Most preferably, the temperature is kept essentially constant within the above-defined ranges.

During the treatment according to (ii), it is further preferred to suitably stir the liquid solvent system. During (ii), the stirring rate is kept essentially constant or changed, the treating with the liquid solvent system according to (ii) thus being carried out at two or more different stirring rates. Most preferably, the B-MWW is suspended in the liquid solvent system at a first stirring rate, and during the treating at the above-described temperatures, the stirring rate is changed, preferably increased. The stirring rates can be suitably chosen depending, for example, on the volume of the liquid solvent system, the amount of the B-MWW employed, the desired temperature, and the like. Preferably, the stirring rate under which the treating of the B-MWW at the above-described temperatures is carried out is in the range of from 50 to 300 r.p.m. (rounds per minute), more preferably from 150 to 270 r.p.m., more preferably from 240 to 260 r.p.m.

According to a conceivable embodiment of the present invention, the treating according to (ii) may be carried out in two or more steps wherein between at least two steps, the zeolitic material obtained from a given treating according to (ii) is subjected to drying, preferably at a temperature in the range of from 90 to 200° C., more preferably from 100 to 150° C., and the thus dried material is subjected to a further treating according to (ii).

As to the individual treating steps according to (ii) and the conditions applied, full reference is made to the conditions as described above. Concerning the treating time, the sum of the treating times of the individual steps are to be understood as the treating time described above. For each of the at least 2 individual treating steps, the same or different treating conditions can be applied. Therefore, the present invention relates to above-defined process and zeolitic material obtainable or obtained therefrom, wherein the treating according to (ii) is carried out in at least 2 separate steps, wherein between at least 2 treating steps, the zeolitic material is dried, preferably at a temperature in the range of from 100 to 150° C. Suitable drying atmospheres include technical nitrogen, air, or lean air.

After the treating according to (ii), the obtained deboronated B-MWW is suitably separated from the suspension. All methods of separating the deboronated B-MWW from the respective suspension are conceivable. These methods include filtration, ultrafiltration, diafiltration and centrifugation methods or, for instance, spray-drying processes and spray granulation processes. A combination of two or more of these methods can be applied. According to the present invention, the deboronated B-MWW is preferably separated from the suspension by filtration. Preferably, a filter cake is obtained which is preferably subjected to washing, preferably with water. If washing is applied, it is preferred to continue the washing process until the washing water has a conductivity of at most 1,000 microSiemens/cm, more preferably of at most 750 microSiemens/cm, more preferably of at most 500 microSiemens/cm In general, the process of the present invention can optionally comprise further steps for the work-up and/or further physical and/or chemical transformation of the deboronated B-MWW obtained in (ii). The obtained zeolitic material can for example be subjected to any sequence of isolation and/or washing procedures, wherein the zeolitic material is preferably subjected to at least one isolation and at least one washing procedure.

After separation of the deboronated B-MWW from the suspension, preferably achieved via filtration, and after washing, the washed filter cake containing the deboronated B-MWW is optionally subjected to drying, for example by subjecting the filter cake to a suitable gas stream such as air, lean air, or nitrogen, preferably a nitrogen stream. Thus, according to a particular preferred embodiment of the present invention, (ii) comprises drying the deboronated B-MWW, the drying preferably being carried out at a temperature in the range of from 100 to 180° C., more preferably from 110 to 140° C. Concerning the duration of drying, no specific restrictions exist. Preferably, drying is carried out for a period in the range of from 1 to 30 h, more preferably from 14 to 18 h. If spray-drying is carried out, it is conceivable to subject the liquid solvent system containing the zeolitic material, optionally after concentration, directly to spray-drying. Further, it is conceivable to subject the separated and washed zeolitic material to spray-drying, optionally after suitable re-suspending of the washed and optionally pre-dried zeolitic material.

Optionally, stage (ii) comprises the calcination of the separated and preferably dried deboronated B-MWW, wherein the calcination is preferably carried out at a temperature in the range of from 400 to 800° C., more preferably from 600 to 700° C. Preferred atmospheres under which the calcination is carried out include technical nitrogen, air, or lean air. Preferred calcination times are in the range of from 0.5 to 12 h, more preferably from 1 to 10 h, more preferably from 2 to 6 h.

The treatment according to (ii) with the liquid solvent system reduces the molar ratio $B_2O_3:SiO_2$ of the zeolitic material framework. Preferably, a deboronated B-MWW is obtained from (ii) having a molar ratio $B_2O_3:SiO_2$ of at most 0.01:1, more preferably in the range of from 0.001:1 to 0.01:1, more preferably from 0.001:1 to 0.009:1, more preferably from 0.001:1 to 0.008:1, more preferably from 0.001:1 to 0.007:1, more preferably from 0.001:1 to 0.006:1, more preferably from 0.001:1 to 0.005:1, more preferably from 0.001:1 to 0.004:1, more preferably from 0.001:1 to 0.003:1.

According to an especially preferred embodiment of the present invention, the zeolitic material obtained from (ii) is in the form of a powder, preferably in the form of a spray powder wherein the spray-powder may result either from spray-drying in (i) and/or spray-drying in (ii), as described above. Preferably, spray-drying is carried out in (i), and no spray-drying is carried out in (ii).

Step (iii)

According to the present invention, the preferably separated and dried, and optionally calcined, deboronated B-MWW obtained from (ii) is further subjected to step (iii) wherein tin is introduced into the material to obtain a tin-containing zeolitic material. In particular, in (iii), tin is introduced into the deboronated B-MWW obtained from (ii) by a process comprising (iii.1) preparing an aqueous synthesis mixture containing the deboronated B-MWW obtained from (ii), an MWW template compound, preferably selected from the group consisting of piperidine, hexamethylene imine, N,N,N,N',N', N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a tin source, wherein in the synthesis mixture, the molar ratio of Sn, calculated as $SnO_2$, relative to Si, calculated as $SiO_2$ and contained in the deboronated B-MWW, is at most 0.015:1;

(iii.2) hydrothermally synthesizing a tin-containing zeolitic material having an MWW-type framework structure from the synthesis mixture obtained from (iii.1) thereby obtaining a tin-containing zeolitic material having an MWW-type framework structure in its mother liquor;

(iii.3) separating the tin-containing zeolitic material having an MWW-type framework structure obtained from (iii.2) from its mother liquor.

As far as the MWW template compound in (iii.3) is concerned, no specific restrictions exist provided that the tin-containing B-MWW is obtained. Preferably, the MWW template compound is selected from the group consisting of piperidine, hexamethylene imine, N,N,N,N',N',N'-hexamethyl-1,5-pentanediammonium ion, 1,4-bis(N-methylpyrrolidinium)-butane, octyltrimethylammonium hydroxide, heptyltrimethylammonium hydroxide, hexyltrimethylammonium hydroxide, and a mixture of two or more thereof. More preferably, the MWW template compound is piperidine.

As far as the tin source used in (iii.1) is concerned, no specific restrictions exist provided that Sn is introduced into the deboronated B-MWW. Preferably, the tin source is selected from the group consisting of Sn(IV) salts, Sn(II) salts and a mixture of two or more thereof, more preferably from the group consisting of $SnCl_4$, Sn(IV)-acetate, Sn(IV)-tert-butoxide, $SnBr_4$, $SnF_4$, Sn(IV)-bisacetylacetonate dichloride; Sn(IV)-bisacetylacetonate dibromide, Sn(II)-acetate, Sn(II)-acetylacetonate, Sn(II)-citrate, $SnCl_2$, $SnF_2$, $SnI_2$, $SnSO_4$, and a mixture of two or more thereof. More preferably, the tin source is Sn(IV)-tert-butoxide or Sn(II)-acetate.

Preferably, the molar ratio of Sn, calculated as $SnO_2$, relative to Si, calculated as $SiO_2$ and contained in the deboronated B-MWW, in the synthesis mixture in (iii.1) is in the range of from 0.001:1 to 0.015:1, more preferably from 0.001:1 to 0.010:1, more preferably from 0.001:1 to 0.0075:1, more preferably from 0.001:1 to 0.005:1. Conceivable preferred ranges are from 0.002:1 to 0.005:1, or from 0.003:1 to 0.005:1, or from 0.004:1 to 0.005:1, or from 0.001:1 to 0.004:1, or from 0.002:1 to 0.004:1, or from 0.003:1 to 0.004:1, or from 0.001:1 to 0.003:1, or from 0.002:1 to 0.003:1, or from 0.001:1 to 0.002:1.

Concerning the molar ratio of the MWW template compound relative to Si contained in the deboronated B-MWW in the synthesis mixture in (iii.1), no specific restrictions exist. Preferably, the molar ratio of the MWW template compound relative to Si, calculated as $SiO_2$ and contained in the deboronated B-MWW, is in the range of from 1.0:1 to 2.0:1, more preferably from 1.2:1 to 1.8:1, more preferably from 1.4:1 to 1.6:1.

Concerning the molar ratio of $H_2O$ relative to Si contained in the deboronated B-MWW in the synthesis mixture in (iii.1), the molar ratio of $H_2O$ relative to Si, calculated as $SiO_2$ and contained in the deboronated B-MWW, no specific restrictions exist. Preferably, the molar ratio of $H_2O$ relative to Si, calculated as $SiO_2$ and contained in the deboronated B-MWW is in the range of from 10:1 to 20:1, preferably from 12:1 to 18:1, more preferably from 14:1 to 16:1.

The synthesis mixture obtained in (iii.1) is subjected to hydrothermally synthesizing a tin-containing zeolitic material having an MWW-type framework structure. It may be conceivable to use at least one suitable seeding material in step (iii.2) to obtain the tin-containing zeolitic material contained in its mother liquor. For example, a conceivable seeding material is a zeolitic material having an MWW framework structure. Preferably, the hydrothermal synthesis according to (iii.2) is carried out at a temperature in the range of from 80 to 250° C., more preferably from 120 to 200° C., more preferably from 160 to 180° C. Further, the hydrothermal synthesizing according to (iii.2) is preferably carried out for a period in the range of from 20 to 200 h, more preferably from 60 to 160 h, more preferably from 110 to 125 h. Preferred ranges are, for example, 20 to 200 h or from 30 to 160 h or from 40 to 125 h.

During the hydrothermal synthesis according to (iii.2), it is preferred to suitably stir the synthesis mixture wherein the stirring rate is kept essentially constant or changed. The stirring rate can be suitably chosen depending, for example, on the volume of the aqueous synthesis mixture, the amount of the zeolitic material employed, the desired temperature, and the like. Preferably, the stirring rate under which the treating of the zeolitic material at the above-described temperatures is carried out is preferably in the range of from 50 to 300 r.p.m. (rounds per minute), more preferably from 70 to 150 r.p.m., more preferably from 90 to 120 r.p.m.

After hydrothermal synthesis, the obtained tin-containing zeolitic material having an MWW-type framework structure is suitably separated from the mother liquor in step (iii.3). All methods of separating the tin-containing zeolitic material having an MWW-type framework structure from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the tin-containing zeolitic material having an MWW-type framework structure is preferably separated from its mother liquor by filtration to obtain a filter cake which is preferably subjected to washing, preferably with water.

Prior to separating the tin-containing zeolitic material having an MWW-type framework structure from its mother liquor, it is possible to increase the tin-containing zeolitic material having an MWW-type framework structure content of the mother liquor by concentrating the suspension. If washing as applied, it is preferred to continue the washing process until the washing water has a conductivity of less than 1,000 microSiemens/cm, more preferably of less than 750 microSiemens/cm, more preferably of less than 500 microSiemens/cm.

After separation of the tin-containing zeolitic material having an MWW-type framework structure from its mother liquor, preferably achieved via filtration, and after washing, the washed filter cake containing the tin-containing zeolitic material having an MWW-type framework structure is optionally subjected to pre-drying, for example by subjecting the filter cake to a suitable gas stream, preferably a nitrogen stream, for a time preferably in the range of from 4 to 10 h, more preferably from 5 to 8 h.

Preferably, stage (iii.3) comprises drying the tin-containing zeolitic material having an MWW-type framework structure, wherein the drying is preferably carried out at a temperature in the range of from 100 to 180° C., more preferably from 110 to 140° C. Concerning the duration of drying the tin-containing zeolitic material having an MWW-type framework structure, no specific restrictions exist. Preferably, the drying is carried out for a period in the range of from 1 to 30 h, more preferably from 6 to 24 h, more preferably from 14 to 18 h.

While it is generally possible to subject the separated and preferably dried tin-containing zeolitic material having an MWW-type framework structure to calcination, it is especially preferred according to the present invention not to subject the separated and preferably dried tin-containing zeolitic material having an MWW-type framework structure obtained in (iii.3) before (iv). In this context, the term "calcination" relates to a heating of the tin-containing zeolitic material having an MWW-type framework structure to a temperature of above 450° C. Thus, according to a particular embodiment of the present invention, the separated and preferably dried tin-containing zeolitic material having an MWW-type framework structure obtained in (iii.3) is not subjected to calcination before (iv).

Step (iv)

According to the present invention, the separated and preferably dried tin-containing zeolitic material having an MWW-type framework structure obtained from (iii) is subjected to stage (iv) wherein the tin-containing zeolitic material having an MWW-type framework structure is treated with an aqueous solution having a pH of at most 5 thereby obtaining the Sn-MWW having an Sn content of less than 2 weight-%, calculated as element and based on the weight of the Sn-MWW, and optionally separating the Sn-MWW from the aqueous solution.

Preferably, in (iv), the tin-containing zeolitic material having an MWW-type framework structure obtained from (iii) is treated with an aqueous solution which comprises an organic acid, preferably selected from the group consisting of oxalic acid, acetic acid, citric acid, methane sulfonic acid, and a mixture of two or more thereof, and/or an inorganic acid, preferably selected from the group consisting of phosphoric acid, sulphuric acid, hydrochloric acid, nitric acid, and a mixture of two or more thereof, the inorganic acid more preferably being nitric acid. Preferably, in (iv), the aqueous solution has a pH in the range of from 0 to 5, more preferably from 0 to 3, more preferably from 0 to 2. The pH values are to be understood as being determined with a pH sensitive glass electrode.

Concerning the temperature of the treating with the aqueous solution according to (iv), no specific restrictions exist. Preferably, in (iv), the tin-containing zeolitic material having an MWW-type framework structure is treated with the aqueous solution at a temperature in the range of from 50 to 175° C., more preferably from 70 to 125° C., more preferably from 95 to 105° C. Preferably, in (iv), the tin-containing zeolitic material having an MWW-type framework structure is treated with the aqueous solution for a period in the range of from 1 to 40 h, more preferably from 12 to 24 h, more preferably from 18 to 22 h.

As far as the weight ratio of the tin-containing zeolitic material having an MWW-type framework structure relative to the aqueous solution is concerned, no specific restrictions exist. Preferably, in (iv), the weight ratio of the aqueous solution relative to the tin-containing zeolitic material having an MWW-type framework structure is in the range of from 10:1 to 50:1, more preferably from 20:1 to 40:1, more preferably from 25:1 to 35:1.

Concerning the type of vessel in which heating in (iv) is conducted, no particular restrictions exist. Preferably, the vessel is suitably selected to allow to treat the zeolitic material at the temperatures described above, at which temperatures the solvent system is in its liquid state. Therefore, as far as higher temperatures are concerned, in (iv), the treating is carried out in a closed system under autogenous pressure.

Further, according to an alternative preferred embodiment of the present invention, in (iv), the treating is carried out in an open system under reflux. Thus, the preferred vessel, representing an open system, used for the treating according to (iv) is preferably equipped with a reflux condenser During the treating according to (iv), it is preferred to suitably stir the aqueous solution containing the zeolitic material. During (iv), the stirring rate is kept essentially constant or changed. The stirring rate can be suitably chosen depending, for example, on the volume of the aqueous solution, the amount of the zeolitic material employed, the desired temperature, and the like. Preferably, the stirring rate under which the treating of the tin-containing zeolitic material having an MWW-type framework structure at the above-described temperatures is carried out is in the range of from 50 to 300 r.p.m. (rounds per minute), more preferably from 100 to 250 r.p.m., more preferably from 180 to 220 r.p.m.

The treatment according to (iv) preferably comprises suitably separating the Sn-MWW from the aqueous solution. All methods of separating Sn-MWW from the aqueous solution are conceivable. These methods include, for example, filtration, ultrafiltration, diafiltration and centrifugation methods or, for instance, spray drying processes and spray granulation processes. A combination of two or more of these methods can be applied. According to the present invention, Sn-MWW is preferably separated from the aqueous solution by filtration to obtain a filter cake which is preferably subjected to washing, preferably with water.

If washing as applied, it is preferred to continue the washing process until the washing water has a pH of 7, wherein the pH is to be understood as being determined using a pH sensitive glass electrode.

Preferably, (iv) comprises drying the Sn-MWW, wherein the drying is preferably carried out at a temperature in the range of from 100 to 180° C., more preferably from 110 to 130° C. Concerning the duration of drying the Sn-MWW, no specific restrictions exist. Preferably, the drying is carried out for a period in the range of from 1 to 20 h, more preferably from 4 to 16 h, more preferably from 8 to 12 h.

Preferably, the separated and preferably dried Sn-MWW is further subjected to calcination in (iv), wherein the calcination is preferably carried out at a temperature in the range of from 400 to 800° C., more preferably from 450 to 700° C., more preferably from 500 to 600° C. Concerning the duration of calcination, no specific restrictions exist. Preferably, the calcination is carried out for a period in the range of from 1 to 20 h, more preferably from 8 to 12 h.

The Novel Sn-MWW

As mentioned above, from (iv) a Sn-MWW is obtained with a tin content calculated as element and based on the weight of the Sn-MWW, of at most 2.0 weight-%. Preferably, the tin content of the novel Sn-MWW is in the range of from 0.05 to 2.0 weight-%, more preferably from 0.1 to 1.9 weight-%, more preferably from 0.1 to 1.8 weight-%, more preferably from 0.1 to 1.7 weight-%, more preferably from 0.1 to 1.6 weight-%, more preferably from 0.1 to 1.5 weight-%, more preferably from 0.1 to 1.4 weight-%, more preferably from 0.1 to 1.3 weight-%, more preferably from 0.1 to 1.2 weight-%, more preferably from 0.1 to 1.0 weight-%. Further preferably, the tin content of the novel Sn-MWW is in the range of from 0.1 to 1.9 weight-%, more preferably from 0.3 to 1.5 weight-%, more preferably from 0.4 to 1.2 weight-%, more preferably from 0.5 to 1.0 weight-%. Further preferably, the tin content of the novel Sn-MWW is in the range of from 0.1 to 1.9 weight-%, more preferably from 0.2 to 1.5 weight-%, more preferably from 0.3 to 1.2 weight-%, more preferably from 0.4 to 1.0 weight-%. Conceivable preferred ranges are, for example, from 0.15 to 0.9 weight-% or from 0.2 to 0.8 weight-% or from 0.25 to 0.7 weight-% or from 0.3 to 0.6 weight-% or from 0.35 to 0.5 weight-%.

Surprisingly, it was found that the process according to the invention which comprises the incorporation of Sn into a deboronated B-MWW, wherein the amount of Sn is chosen in such a manner that the Sn-MWW obtained from (iv) has a Sn content of at most 2 weight-%, leads to a novel tin-containing zeolitic material having an MWW-type framework structure. Compared to the conventional tin-containing zeolitic material having an MWW framework structure, the novel material is characterized in that it exhibits an increased interlayer distance between the individual layers of the zeolitic material. A specific feature of the novel tin-containing zeolitic material having an MWW-type framework structure is an additional peak in the XRD diffraction pattern at a 2 theta diffraction angle of $(6.6\pm0.1)°$.

Therefore, the present invention generally relates to a tin-containing zeolitic material having an MWW-type framework structure and having an X-ray diffraction pattern comprising a peak at a 2 theta diffraction angle of (6.6±0.1)°, preferably having an X-ray diffraction pattern comprising a peak at a 2 theta diffraction angle of (6.6±0.1)°, a peak at a 2 theta diffraction angle of (7.1±0.1)°, and a peak at a 2 theta diffraction angle of (7.9±0.1)°, more preferably an X-ray diffraction pattern comprising peaks at 2 theta diffraction angles of (6.6±0.1)°, (7.1±0.1)°, (7.9±0.1)°, (9.6±0.1)°, (12.8±0.1)°, (14.4±0.1)°, (14.7±0.1)°, (15.8±0.1)°, (19.3±0.1)°, (20.1±0.1)°, (21.7±0.1)°, (21.9±0.1)°, (22.6±0.1)°, (22.9±0.1)°, (23.6±0.1)°, (25.1±0.1)°, (26.1±0.1)°, (26.9±0.1)°, (28.6±0.1)°, and (29.1±0.1)°.

This increased interlayer distance is further reflected in the c parameter, determined via XRD, which, for the novel Sn-MWW, is (27.1±0.2) Angstrom. Compared to the conventional tin-containing zeolitic materials having MWW framework structure, the c parameter of the novel Sn-MWW is increased.

Preferably, the framework structure of the novel Sn-MWW comprises $SiO_2$ and $B_2O_3$ and the molar ratio $B_2O_3:SiO_2$ is at most 0.01:1, more preferably in the range of from 0.001:1 to 0.01:1, more preferably from 0.001:1 to 0.009:1, more preferably from 0.001:1 to 0.008:1, more preferably from 0.001:1 to 0.007:1, more preferably from 0.001:1 to 0.006:1, more preferably from 0.001:1 to 0.005:1, more preferably from 0.001:1 to 0.004:1, more preferably from 0.001:1 to 0.003:1.

Preferably, at least 95 weight-%, preferably at least 98 weight-%, more preferably at least 99 weight-%, more preferably at least 99.5 weight-%, more preferably at least 99.9 weight-% of the framework structure of the novel Sn-MWW consist of $SiO_2$ and $B_2O_3$ and optionally Sn. In particular, the Sn-MWW is free of aluminum which, in the context of the present invention, relates to a Sn-MWW which may contain aluminum only in traces as impurity.

Preferably, the novel Sn-MWW has a BET surface area, determined according to DIN 66131, in the range of from 300 to 600 m²/g, more preferably from 350 to 550 m²/g, more preferably from 350 to 500 m²/g. Preferably, the novel Sn-MWW has a Langmuir surface, determined according to DIN 66131, in the range of from 400 to 800 m²/g, more preferably from 400 to 750 m²/g, such as from 400 to 700 m²/g or from 500 to 600 m²/g.

As mentioned above, it is preferred that in at least one stage of the preferred process for the preparation of the novel Sn-MWW, a spray-drying step is performed. Therefore, it is preferred that the novel Sn-MWW is present in the form of a spray-powder obtained from such spray-drying. Such a spray-powder can be characterized by the Dv10 value, Dv50 value, and/or the Dv90 value, which values are typically at least 1 micrometer. Typical values for Dv10 may be in the range of from 1 to 10 micrometer, typical values for Dv50 may be in the range of from 5 to 50 micrometer, typical values for Dv90 may be in the range of from 20 to 100 micrometer. In this context, the Dv10, Dv50 and Dv90 values are to be understood as being determined according to a method where 1.0 g of a given spray-powder is suspended in 100 g deionized water and stirred for 1 min and then subjected to the measurement in a particle size measurement apparatus Mastersizer S long bed version 2.15, ser. No. 33544-325; (supplier: Malvern Instruments GmbH, Herren-berg, Germany) with the following parameters: focal width 300 RF mm; beam length 10.00 mm; module MS17; shadowing 16.9%; dispersion model 3$$D; analysis model polydisperse; correction none.

Further Steps

Treatment of the Sn-MWW with an Aqueous System

Further, it is conceivable that the Sn-MWW obtained from (iv), preferably the separated, dried and calcined Sn-MWW, is subjected to a treatment with an aqueous system having a pH in the range of from 5.5 to 8.

Preferably, the Sn-MWW is treated with the aqueous system at a temperature in the range of from 80 to 220° C., preferably from 100 to 180° C., more preferably from 130 to 150° C. Further, the treating with the aqueous system is preferably carried out for a period in the range of from 1 to 20 h, more preferably from 4 to 15 h, more preferably from 6 to 10 h. Preferably, at least 95 weight-%, more preferably at least 99 weight-%, more preferably at least 99.9 weight-% of the aqueous system consist of water. More preferably, the aqueous system is water.

According to a preferred embodiment of the present invention, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the Sn-MWW with the aqueous system, the Sn-MWW is preferably suitably separated from the suspension. All methods of separating the Sn-MWW from the suspension are conceivable. These methods include, for example, filtration, ultrafiltration, diafiltration and centrifugation methods or, for instance, spray drying processes and spray granulation processes. A combination of two or more of these methods can be applied. According to the present invention, the Sn-MWW is preferably separated from the suspension by filtration, and the thus obtained Sn-MWW, for example in the form of a filter cake, is preferably subjected to washing, preferably to washing with water, at a temperature in the range of from up to 50° C., more preferably from 15 to 35° C., more preferably from 20 to 30° C. Subsequently, the filter cake, optionally further processed to obtained a suitable suspension, is optionally subjected to spray-drying or to ultrafiltration.

After treating with the aqueous system, the Sn-MWW is preferably subjected to drying and/or calcination, wherein drying is preferably carried out at a temperature in the range of from 100 to 180° C., preferably from 130 to 150° C., for a period in the range of from 10 to 70 h, preferably from 15 to 25 h, and calcination is preferably carried out at a temperature in the range of from 550 to 700° C., preferably from 600 to 680° C., for a period in the range of from 1 to 10 h, preferably from 2 to 5 h.

Therefore, the present invention also relates to the above defined process, further comprising (iv.1) treating the Sn-MWW obtained from (iv) with an aqueous system having a pH in the range of 5.5 to 8;

(iv.2) drying and/or calcining the Sn-MWW obtained from (iv.1).

Preparation of a Molding

Depending on the specific use of the novel Sn-MWW, it is conceivable that the powder or the spray-powder obtained from (iv), optionally from (iv.1) or (iv.2) is further processed to prepare a molding comprising the powder or the spray-powder.

Therefore, the present invention also relates to the above-defined process, further comprising (v) preparing a moldable mixture comprising the Sn-MWW obtained from (iv), the moldable mixture optionally comprising a binder or a binder precursor;

(vi) subjecting the mixture obtained from (v) to shaping to obtain a molding containing the Sn-MWW;

(vii) optionally drying and/or calcining the molding obtained in (vi).

In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organo-metallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaolin, hectorite, bentonites, halloysites, dickites, nacrites or anaxites. These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. This silica may be amorphous silica, the size of the silica particles being, for example, in the range of from 5 to 100 nm and the surface area of the silica particles being in the range of from 50 to 500 $m^2$/g. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica can be preferred.

As to the ratio of the amount of Sn-MWW relative to the amount of binder used for preparing a molding, it generally can be freely chosen. Generally, the weight ratio of the Sn-MWW relative to binder is in the range of from 20:1 to 1:20, preferably from 10:1 to 1:10, more preferably from 1:1 to 1:10.

For preparing a molding based on the Sn-MWW, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinyl pyrrolidone, polyisobutene or poly-tetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. Preferably, the at least one pasting agent is removed by drying and/or calcination, as further described below.

As to the ratio of the amount of Sn-MWW relative to the amount of pasting agent used for preparing a molding, it generally can be freely chosen. Generally, the weight ratio of the Sn-MWW relative to pasting agent is in the range of from 20:1 to 1:50, preferably from 10:1 to 1:40, more preferably from 1:1 to 1:30.

It is further conceivable that a pore-forming agent, in particular a mesopore-forming agent is additionally employed for the preparation of the moldings. Such pore forming agents usually employed are preferably polymeric vinyl compounds, such as, for example, polyalkylene oxides, such as polyethylene oxides, polystyrenes, polyacrylates, polymethacrylates, polyolefins, polyamides and polyesters.

The moldings of the present invention may be shaped in (vi) in every conceivable geometry such as strands, for example having rectangular, triangular hexagonal, quadratic, oval, or circular cross-section, stars, tablets, spheres, hollow cylinders, and the like. Depending on the specific geometry, the shaping process according to (vi) will be chosen.

If, according to a preferred embodiment of the present invention, strands are prepared, the shaping according to (vi) preferably comprises subjecting the mixture obtained in (v) to extrusion. Suitable extrusion apparatuses are described, for example, in "Ullmann's Enzyklopädie der Technischen Chemie", 4th edition, vol. 2, page 295 et seq., 1972. In addition to the use of an extruder, an extrusion press can also be used for the preparation of the moldings. If necessary, the extruder can be suitably cooled during the extrusion process. Extrusion processes are conceivable wherein per batch, the power consumption is in the range of from 1 to 10 A, preferably from 1.5 to 6 A, more preferably from 2 to 4 A. The strands leaving the extruder via the extruder die head can be mechanically cut by a suitable wire or via a discontinuous gas stream.

The molding obtained from (vi) is optionally dried and/or calcined. No specific restrictions exist concerning the drying and calcination conditions. The drying is preferably carried out at temperatures in the range of in general from 80 to 160° C., more preferably from 90 to 155° C., more preferably from 100 to 150° C., and preferably for a duration in the range of from 6 to 24 h, more preferably from 8 to 20 h such as from 10 to 20 h. The drying can be effected under any suitable gas atmosphere, wherein nitrogen, air and/or lean air are preferred.

The calcination is preferably carried out at temperatures in the range of in general from 400 to 650° C., more preferably from 450 to 625° C., more preferably from 500 to 600° C., and preferably for a duration in the range of from 0.25 to 6 h, more preferably from 0.5 to 5 h such as from 0.5 to 2 h. The calcination can be effected under any suitable gas atmosphere, wherein air and/or lean air are preferred.

Therefore, the present invention also relates to a molding, preferably an extrudate, comprising the novel Sn-MWW according to the present invention and optionally at least one binder.

Treatment of the Moldings with an Aqueous System

Further, it is conceivable that the moldings comprising the Sn-MWW obtained from (vi) or (vii), preferably (vii), are subjected to a treatment with an aqueous system having a pH in the range of 5.5 to 8.

Preferably, the moldings are treated with the aqueous system at a temperature in the range of from 80 to 220° C., preferably from 100 to 180° C., more preferably from 130 to 150° C. Further, the treating with the aqueous system is carried out for a period in the range of from 1 to 20 h, preferably from 4 to 15 h, more preferably from 6 to 10 h. Preferably, at least 95 weight-%, more preferably at least 99 weight-%, more preferably at least 99.9 weight-% of the aqueous system consists of water. More preferably, the aqueous system is water.

According to a preferred embodiment of the present invention, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the moldings with the aqueous system, the moldings are preferably suitably separated from the suspension. All methods of separating the moldings from the suspension are conceivable. These methods include, for example, filtration and centrifugation methods. A combination of two or more of these methods can be applied. According to the present invention, the moldings are preferably separated from the aqueous system by filtration, and the thus obtained moldings are preferably subjected to washing, preferably to washing with water, at a temperature in the range of from up to 50° C., preferably from 15 to 35° C., more preferably from 20 to 30° C.

After treating with the aqueous system, the moldings are preferably subjected to drying and/or calcination, wherein drying is preferably carried out at a temperature in the range of from 100 to 180° C., more preferably from 130 to 150° C., preferably for a period in the range of from 10 to 70 h, more preferably from 15 to 25 h, and calcination is preferably carried out at a temperature in the range of from 550 to 700° C., more preferably from 600 to 680° C., preferably for a period in the range of from 1 to 10 h, more preferably from 2 to 5 h.

Therefore, the present invention also relates to the above defined process, further comprising
(viii) treating the moldings obtained from (vi) or (vii), preferably (vii), with an aqueous system having a pH in the range of 5.5 to 8;
(ix) optionally drying and/or calcining the moldings obtained from (viii).

Generally, the present invention further relates to a zeolitic material, optionally contained in a molding, obtainable or obtained by a process according to the present invention.

Further, the present invention relates to a molding, comprising the zeolitic material of the present invention or the zeolitic material obtainable or obtained by the process of the present invention, said molding optionally additionally comprising a binder, preferably a silica binder.

Preferred Uses

The tin-containing zeolitic material having an MWW-type framework structure (Sn-MWW) according to the invention, preferably obtainable or obtained by the process according to the invention, and/or the moldings of the present invention comprising the tin-containing zeolitic material having an MWW-type framework structure (Sn-MWW) according to the invention, preferably obtainable or obtained by the process according to the invention generally, can be used for every conceivable purpose such as a catalytically active agent, a catalyst support, a molecular sieve, an adsorbent, a filler, and the like.

According to a preferred embodiment of the present invention, the Sn-MWW according to the present invention or the Sn-MWW obtainable or obtained by the process of the present invention is used as a catalyst or a catalyst component, more preferably as a catalyst in oxidation reactions, more preferably as a catalyst for a Baeyer-Villiger-type oxidation reaction. Thus, the present invention also relates to an oxidation process, preferably a Baeyer-Villiger-type oxidation process, wherein the Sn-MWW according to the present invention or the Sn-MWW obtainable or obtained by the process of the present invention is used as a catalyst or a catalyst component.

Therefore, the present invention also relates to the use of the Sn-MWW according to the present invention or the Sn-MWW obtainable or obtained by the process of the present invention as catalyst in a process for the oxidation of an organic carbonyl compound according to formula (I)

(I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, said process comprising
(i) reacting the compound of formula (I), optionally in the presence of a solvent, with hydrogen peroxide in the presence of the Sn-MWW according to the present invention or the Sn-MWW obtainable or obtained by the process of the present invention, preferably at a temperature in the range of from 50 to 150° C., preferably from 70 to 120° C., more preferably from 90 to 110° C., to obtain a compound of formula (II)

(II)

wherein, if neither $R_1$ nor $R_2$ is a hydrogen atom, $R_1$ and $R_2$ may form, together with the carbonyl group or the carboxyl group, a ring and the compound of formula (I) is

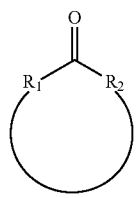

and the compound of formula (II) is

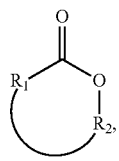

(ii) optionally separating the compound of formula (II) from the mixture obtained in (i); preferably wherein $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom and wherein, if neither $R_1$ nor $R_2$ is a hydrogen atom, $R_1$ and $R_2$ may form, together with the carbonyl group or the carboxyl group, a ring having from 4 to 20 carbon atoms.

Further, the present invention relates to a process for the oxidation of an organic carbonyl compound according to formula (I)

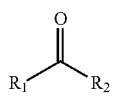
(I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, said process comprising (i) reacting the compound of formula (I), optionally in the presence of a solvent, with hydrogen peroxide in the presence of the Sn-MWW according to the present invention or the Sn-MWW obtainable or obtained by the process of the present invention, preferably at a temperature in the range of from 50 to 150° C., preferably from 70 to 120° C., more preferably from 90 to 110° C., to obtain a compound of formula (II)

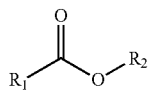
(II)

wherein, if neither $R_1$ nor $R_2$ is a hydrogen atom, $R_1$ and $R_2$ may form, together with the carbonyl group or the carboxyl group, a ring and the compound of formula

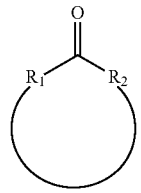

and the compound of formula (II) is

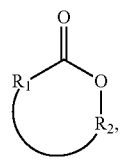

(ii) optionally separating the compound of formula (II) from the mixture obtained in (i); preferably wherein $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom and wherein, if neither $R_1$ nor $R_2$ is a hydrogen atom, $R_1$ and $R_2$ may form, together with the carbonyl group or the carboxyl group, a ring having from 4 to 20 carbon atoms.

The present invention is also characterized by the following embodiments and the combinations of embodiments as indicated by the respective dependencies:

1. A process for preparing a tin-containing zeolitic material having an MWW-type framework structure (Sn-MWW) comprising
   (i) providing a boron-containing zeolitic material having an MWW framework structure comprising $SiO_2$ and $B_2O_3$ (B-MWW);
   (ii) deboronating the B-MWW by treating the B-MWW provided in (i) with a liquid solvent system having a pH in the range of from 5.5 to 8;
   (iii) incorporating Sn into the deboronated B-MWW obtained from (ii) by a process comprising
      (iii.1) preparing an aqueous synthesis mixture containing the deboronated B-MWW obtained from (ii), an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a tin source, wherein in the synthesis mixture, the molar ratio of Sn, calculated as $SnO_2$, relative to Si, calculated as $SiO_2$ and contained in the deboronated B-MWW, is at most 0.015:1;
      (iii.2) hydrothermally synthesizing a tin-containing zeolitic material having an MWW-type framework structure from the synthesis mixture obtained from (iii.1) thereby obtaining a tin-containing zeolitic material having an MWW-type framework structure in its mother liquor;
      (iii.3) separating the tin-containing zeolitic material having an MWW-type framework structure obtained from (iii.2) from its mother liquor;
   (iv) treating the tin-containing zeolitic material having an MWW-type framework structure obtained from (iii) with an aqueous solution having a pH of at most 5 thereby obtaining the Sn-MWW having an Sn content of at most 2 weight-%, calculated as element and based on the weight of the Sn-MWW, and optionally separating the Sn-MWW from the aqueous solution.

2. The process of embodiment 1, wherein in (i), the B-MWW is provided by a process comprising
   (a) hydrothermally synthesizing a B-MWW precursor from an aqueous synthesis mixture containing a silicon source, preferably ammonia stabilized colloidal silica, a boron source, preferably boric acid, and an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyl-trimethylammonium hydroxide, and a mixture of two or more thereof, to obtain the B-MWW precursor in its mother liquor;
   (b) separating the B-MWW precursor from its mother liquor, preferably comprising drying the B-MWW precursor, wherein the drying is preferably carried out at a temperature in the range of from 100 to 180° C., more preferably from 110 to 140° C., wherein in the synthesis mixture in (a), the molar ratio of B, calculated as $B_2O_3$ and contained in the boron source, relative to Si, calculated as $SiO_2$ and contained in the Si source, is preferably in the range of from 0.4:1 to 0.6:1, more preferably from 0.45:1 to 0.55:1, more preferably from 0.47:1 to 0.52:1;

the molar ratio of the MWW template compound, relative to Si, calculated as $SiO_2$ and contained in the Si source, is preferably in the range of from 0.8:1 to 1.7:1, more preferably from 1.0:1 to 1.5:1, more preferably from 1.1:1 to 1.3:1; and the molar ratio of $H_2O$ relative to Si, calculated as $SiO_2$ and contained in the Si source, is preferably in the range of from 12:1 to 20:1, more preferably from 13:1 to 18:1, more preferably from 14:1 to 16:1.

3. The process of embodiment 2, wherein (b) comprises spray-drying the B-MWW precursor.

4. The process of embodiment 2, wherein the drying is carried out for a period in the range of from 1 to 10 h, more preferably from 2 to 6 h.

5. The process of any of embodiments 2 to 4, wherein (b) comprises calcination of the separated and preferably dried B-MWW precursor to obtain the B-MWW, wherein the calcination is preferably carried out at a temperature in the range of from 400 to 800° C., more preferably from 600 to 700° C.

6. The process of embodiment 5, wherein the calcination is carried out for a period in the range of from 1 to 10 h, more preferably from 2 to 6 h.

7. The process of any of embodiments 1 to 6, wherein in (i), at least 95 weight-%, preferably at least 98 weight-%, more preferably at least 99 weight-% of the framework structure of the B-MWW consist of $B_2O_3$ and $SiO_2$.

8. The process any of embodiments 1 to 7, wherein in (i), the molar ratio $B_2O_3:SiO_2$ of the B-MWW is at least 0.03:1, preferably in the range of from 0.03:1 to 0.09:1, more preferably from 0.03:1 to 0.08:1, more preferably from 0.03:1 to 0.07:1.

9. The process of any of embodiments 1 to 8, wherein in (ii), the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, wherein preferably, the liquid solvent system does not contain an inorganic or organic acid, or a salt thereof.

10. The process of any of embodiments 1 to 9, wherein in (ii), the weight ratio of the liquid solvent system relative to B-MWW is in the range of from 40:1 to 5:1, preferably from 30:1 to 7:1, more preferably from 20:1 to 10:1.

11. The process of any of embodiments 1 to 10, wherein in (ii), the treating is carried out at a temperature in the range of from 50 to 125° C., preferably from 90 to 115° C., more preferably from 95 to 105° C.

12. The process of any of embodiments 1 to 11, wherein in (ii), the treating is carried out for a period in the range of from 6 to 20 h, preferably from 7 to 17 h, more preferably from 8 to 12 h.

13. The process of any of embodiments 1 to 12, wherein in (ii), the treating is carried out in a closed system under autogenous pressure.

14. The process of any of embodiments 1 to 12, wherein in (ii), the treating is carried out in an open system under reflux.

15. The process of any of embodiments 1 to 14, wherein (ii) comprises drying the deboronated B-MWW, the drying preferably being carried out at a temperature in the range of from 100 to 180° C., more preferably from 110 to 140° C.

16. The process of embodiment 15, wherein (ii) comprises spray-drying the deboronated B-MWW.

17. The process of embodiment 15, wherein the drying is carried our for a period in the range of from 1 to 30 h, preferably from 14 to 18 h.

18. The process of any of embodiments 1 to 17, wherein (ii) comprises calcination of the separated and preferably dried deboronated B-MWW, wherein the calcination is preferably carried out at a temperature in the range of from 400 to 800° C., more preferably from 600 to 700° C.

19. The process of any of embodiments 1 to 18, wherein the deboronated B-MWW has a molar ratio $B_2O_3:SiO_2$ of at most 0.01:1, preferably in the range of from 0.001:1 to 0.01:1, more preferably from 0.001:1 to 0.003:1.

20. The process of any of embodiments 1 to 19, wherein the template compound used in (iii.1) is piperidine.

21. The process of any of embodiments 1 to 20, wherein the tin source is selected from the group consisting of $SnCl_4$, Sn(IV)-acetate, Sn(IV)-tert-butoxide, $SnBr_4$, $SnCl_4$, $SnF_4$, Sn(IV)-bisacetylacetonate dichloride; Sn(IV)-bisacetylacetonate dibromide, Sn(II)-acetate, Sn(II)acetylacetonate, Sn(II)-citrate, $SnCl_2$, $SnF_2$, $SnI_2$, $SnSO_4$, and a mixture of two or more thereof, the tin source preferably being Sn(IV)-tert-butoxide.

21. The process of any of embodiments 1 to 20, wherein in the synthesis mixture in (iii.1), the molar ratio of Sn, calculated as $SnO_2$, relative to Si, calculated as $SiO_2$ and contained in the deboronated B-MWW, is in the range of from 0.001:1 to 0.015:1, preferably from 0.001:1 to 0.010:1, more preferably from 0.001:1 to 0.0075:1, more preferably from 0.001:1 to 0.005:1.

22. The process of any of embodiments 1 to 21, wherein in the synthesis mixture in (iii.1), the molar ratio of the MWW template compound relative to Si, calculated as $SiO_2$ and contained in the deboronated B-MWW, is in the range of from 1.0:1 to 2.0:1, preferably from 1.2:1 to 1.8:1, more preferably from 1.4:1 to 1.6:1.

23. The process of any of embodiments 1 to 22, wherein in the synthesis mixture in (iii.1), the molar ratio of $H_2O$ relative to Si, calculated as $SiO_2$ and contained in the deboronated B-MWW, is in the range of from 10:1 to 20:1, preferably from 12:1 to 18:1, preferably from 14:1 to 16:1.

24. The process of any of embodiments 1 to 23, wherein the hydrothermal synthesizing according to (iii.2) is carried out at a temperature in the range of from 80 to 250° C., preferably from 120 to 200° C., more preferably from 160 to 180° C.

25. The process of any of embodiments 1 to 24, wherein the hydrothermal synthesizing according to (iii.2) is carried out for a period in the range of from 20 to 200 h, more preferably from 60 to 160 h, more preferably from 110 to 125 h.

26. The process of any of embodiments 1 to 25, wherein (iii.3) comprises drying the tin-containing zeolitic material having an MWW-type framework structure, wherein the drying is preferably carried out at a temperature in the range of from 100 to 180° C., more preferably from 110 to 140° C.

27. The process of embodiment 26, wherein (iii.3) comprises spray-drying the tin-containing zeolitic material having an MWW-type framework structure.

28. The process of embodiment 26, wherein the drying is carried out for a period in the range of from 1 to 30 h, preferably from 6 to 24 h, more preferably from 14 to 18 h.

29. The process of any of embodiments 1 to 28, wherein in (iii.3) and before (iv), the separated and preferably dried tin-containing zeolitic material having an MWW-type framework structure is not subjected to calcination.
30. The process of any of embodiments 1 to 29, wherein in (iv), the aqueous solution comprises an organic acid, preferably selected from the group consisting of oxalic acid, acetic acid, citric acid, methane sulfonic acid, and a mixture of two or more thereof, and/or an inorganic acid, preferably selected from the group consisting of phosphoric acid, sulphuric acid, hydrochloric acid, nitric acid, and a mixture of two or more thereof, the inorganic acid more preferably being nitric acid.
31. The process of any of embodiments 1 to 30, wherein in (iv), the aqueous solution has a pH in the range of from 0 to 5, preferably from 0 to 3, more preferably from 0 to 2.
32. The process of any of embodiments 1 to 31, wherein in (iv), the tin-containing zeolitic material having an MWW-type framework structure is treated with the aqueous solution at a temperature in the range of from 50 to 175° C., preferably from 70 to 125° C., more preferably from 95 to 105° C.
33. The process of any of embodiments 1 to 32, wherein in (iv), the tin-containing zeolitic material having an MWW-type framework structure is treated with the aqueous solution for a period in the range of from 1 to 40 h, more preferably from 12 to 24 h, more preferably from 18 to 22 h.
34. The process of any of embodiments 1 to 33, wherein in (iv), the weight ratio of the aqueous solution relative to the tin-containing zeolitic material having an MWW-type framework structure is in the range of from 10:1 to 50:1, preferably from 20:1 to 40:1, more preferably from 25:1 to 35:1.
35. The process of any of embodiments 1 to 34, wherein in (iv), the treating is carried out in a closed system under autogenous pressure.
36. The process of any of embodiments 1 to 34, wherein in (ii), the treating is carried out in an open system under reflux.
37. The process of any of embodiments 1 to 36, wherein the tin content of the Sn-MWW obtained from (iv), calculated as element and based on the weight of the Sn-MWW, is in the range of from 0.1 to 1.9 weight-%, more preferably from 0.2 to 1.5 weight-%, more preferably from 0.3 to 1.2 weight-%, more preferably from 0.4 to 1.0 weight-%.
38. The process of any of embodiments 1 to 37, wherein (iv) comprises drying the Sn-MWW, wherein the drying is preferably carried out at a temperature in the range of from 100 to 180° C., more preferably from 110 to 130° C.
39. The process of embodiment 38, wherein (iv) comprises spray-drying the Sn-MWW.
40. The process of embodiment 38, wherein the drying is carried out for a period in the range of from 1 to 20 h, preferably from 4 to 16 h, more preferably from 8 to 12 h.
41. The process of any of embodiments 1 to 40, wherein (iv) comprises calcination of the preferably separated and preferably dried Sn-MWW, wherein the calcination is preferably carried out at a temperature in the range of from 400 to 800° C., more preferably from 450 to 700° C., more preferably from 500 to 600° C.
42. The process of embodiment 41, wherein the calcination is carried out for a period in the range of from 1 to 20 h, more preferably from 8 to 12 h.
43. The process of any of embodiments 1 to 42, further comprising
  (v) preparing a moldable mixture comprising the Sn-MWW obtained from (iv), the moldable mixture optionally comprising a binder or a binder precursor, preferably a silica binder or a silica binder precursor;
  (vi) subjecting the mixture obtained from (v) to shaping to obtain a molding containing the Sn-MWW;
  (vii) optionally drying and/or calcining the molding obtained in (v).
44. The process of embodiment 43, wherein in (vi), the moldable mixture is shaped by extruding.
45. A tin containing zeolitic material having an MWW-type framework structure (Sn-MWW), having a tin content of at most 2 weight-%, calculated as element and based on the weight of the Sn-MWW, and having an X-ray diffraction pattern comprising a peak at a 2 theta diffraction angle of $(6.6\pm0.1)°$, preferably a peak at a 2 theta diffraction angle of $(6.6\pm0.1)°$, a peak at a 2 theta diffraction angle of $(7.1\pm0.1)°$, and a peak at a 2 theta diffraction angle of $(7.9\pm0.1)°$.
46. The zeolitic material of embodiment 45, wherein the zeolitic material has a tin content in the range of from 0.1 to 1.9 weight-%, more preferably from 0.2 to 1.5 weight-%, more preferably from 0.3 to 1.2 weight-%, more preferably from 0.4 to 1.0 weight-%, calculated as element and based on the weight of the Sn-MWW.
47. The zeolitic material of embodiment 45 or 46, having an X-ray diffraction pattern comprising peaks at 2 theta diffraction angles of $(6.6\pm0.1)°$, $(7.1\pm0.1)°$, $(7.9\pm0.1)°$, $(9.6\pm0.1)°$, $(12.8\pm0.1)°$, $(14.4\pm0.1)°$, $(14.7\pm0.1)°$, $(15.8\pm0.1)°$, $(19.3\pm0.1)°$, $(20.1\pm0.1)°$, $(21.7\pm0.1)°$, $(21.9\pm0.1)°$, $(22.6\pm0.1)°$, $(22.9\pm0.1)°$, $(23.6\pm0.1)°$, $(25.1\pm0.1)°$, $(26.1\pm0.1)°$, $(26.9\pm0.1)°$, $(28.6\pm0.1)°$, and $(29.1\pm0.1)°$.
48. The zeolitic material of any of embodiments 45 to 47, wherein the c parameter, as determined via XRD, is $(27.1\pm0.2)$ Angstrom.
49. The zeolitic material of any of embodiments 45 to 48, wherein the MWW-type framework structure of the Sn-MWW comprises $SiO_2$ and $B_2O_3$ and the molar ratio $B_2O_3:SiO_2$ is at most 0.01:1, preferably in the range of from 0.001:1 to 0.01:1, more preferably from 0.001:1 to 0.003:1.
50. The zeolitic material of any of embodiments 45 to 49, wherein at least 95 weight-%, preferably at least 98 weight-%, more preferably at least 99 weight-% of the MWW-type framework structure of the Sn-MWW consist of $SiO_2$ and $B_2O_3$ and optionally Sn.
51. The zeolitic material of any of embodiments 45 to 50, having a BET surface area, determined according to DIN 66131, in the range of from 300 to 600 $m^2/g$, preferably from 350 to 550 $m^2/g$.
52. The zeolitic material of any of embodiments 45 to 51, having a Langmuir surface, determined according to DIN 66131, in the range of from 400 to 800 $m^2/g$, preferably from 400 to 750 $m^2/g$.
53. The zeolitic material of any of embodiments 45 to 52, obtainable or obtained by a process according to any of embodiments 1 to 42, or a zeolitic material obtainable or obtained by a process according to any of embodiments 1 to 42.
54. The zeolitic material of any of embodiments 45 to 53 as a spray-powder.
55. The zeolitic material of any of embodiments 45 to 54 being comprised in a molding, said molding preferably additionally comprising a binder, preferably a silica binder.

56. Use of a zeolitic material according to any of embodiments 45 to 55 as a catalyst, preferably as a catalyst in oxidation reactions, more preferably as a catalyst for the Baeyer-Villiger-type oxidation.

The present invention is further illustrated by the following Examples and Comparative Examples.

EXAMPLES

Example 1

Preparation of a Novel Sn-MWW (i) Preparation of a B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piped-dine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW precursor had a pH of 11.3 as determined via measurement with a pH-sensitive electrode. From said suspension, the B-MWW precursor was separated by filtration. The filter cake was then washed with de-ionized water at room temperature until the washing water had a conductivity of less than 700 microSiemens/cm. The thus obtained filter cake was subjected to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m²
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 600° C. for 10 h. The calcined material had a molar ratio $B_2O_3:SiO_2$ molar ratio of 0.06:1.

(ii) Deboronation 9 kg of de-ionized water and 600 g of the calcined zeolitic material obtained according to Example 1 (i) were refluxed at 100° C. under stirring at 250 r.p.m. for 10 h. The resulting deboronated zeolitic material was separated from the suspension by filtration and washed with 4 l deionized water at room temperature. After the filtration, the filter cake was dried at a temperature of 120° C. for 16 h.

The dried zeolitic material having an MWW framework structure had a $B_2O_3:SiO_2$ molar ratio of 0.0020:1.

(iii) Incorporation of Sn 776.25 g deionized water were provided in a glass beaker and 280 g piperidine were added under stirring and further stirred for 20 minutes. Separately, in a glovebox 5 g tin(IV)-tert-butoxyde were dissolved in 95 g piperidine under nitrogen atmosphere. The mixture was added to the aqueous piperidine suspension and further stirred for 10 minutes. 172.4 g zeolitic material obtained according to Example 1 (ii) were added to the mixture and stirred for 1 h (200 r.p.m.) at room temperature. The obtained suspension was than filled in an autoclave. The mixture was treated for 120 h at a temperature of 170° C. under stirring (100 r.p.m.).

Afterwards the autoclave was cooled down to room temperature and the resulting zeolitic material was separated from the suspension by filtration at room temperature and washed with deionized water until the washing water had a conductivity of less than 300 microSiemens/cm. After the filtration, the filter cake was dried at a temperature of 120° C. for 16 h.

The dried zeolitic material had a Si content of 37 weight-% and a Sn content of 0.68 weight-%

(iv) Acid Treatment 170 g zeolitic material obtained according to Example 1 (iii) were provided in a round bottom flask and 5.1 kg of a 30 weight-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h.

The dried and cacined zeolitic material had a Si content of 43.5 weight-% and a Sn content of 0.78 weight-% and a c parameter as determined via XRD of 27.069 Angstrom. Further, the zeolitic material had a BET surface area, determined according to DIN 66131 of 475 m²/g, a Langmuir surface, determined according to DIN 66131 of 657 m²/g and a total pore area of 189.42 m²/g. Furthermore, the obtained zeolitic material had a X-ray diffraction pattern comprising peaks at 2 theta diffraction angles of (6.6±0.1)°, (7.1±0.1)°, (7.9±0.1)°, (9.6±0.1)°, (12.8±0.1)°, (14.4±0.1)°, (14.7±0.1)°, (15.8±0.1)°, (19.3±0.1)°, (20.1±0.1)°, (21.7±0.1)°, (21.9±0.1)°, (22.6±0.1)°, (22.9±0.1)°, (23.6±0.1)°, (25.1±0.1)°, (26.1±0.1)°, (26.9±0.1)°, (28.6±0.1)°, and (29.1±0.1)°.

Results of Example 1

According to the present invention, a tin-containing zeolitic material was prepared in Example 1 by a combination of a deboronation with the incorporation of Sn and subsequent treating with an acidic solution, wherein the molar ratio of Sn relative to Si was chosen in such a manner that the finally obtained Sn-MWW had a tin-content of at most 2 weight-%. This combination led to a tin-containing zeolitic material having an MWW-type framework structure (Sn-MWW), wherein the X-ray diffraction pattern comprises a peak at a 2 theta diffraction angle of (6.6±0.1)°, which indicates a higher interlayer distance between the layers of the tin-containing zeolitic material. This interlayer distance is ex-pressed by the lattice parameter c of the framework structure, which has a value of 27.069 Angstrom.

Example 2

Preparation of a Novel Sn-MWW (i) Preparation of a B-MWW 470.4 kg de-ionized water were provided in a vessel. Under stirring at 70 rpm (rounds per minute), 162.5 kg boric acid were suspended in the water at room temperature. The suspension was stirred for another 3 h at room temperature. Subsequently, 272.5 kg piperidine were added, and the mixture was stirred for another hour. To the resulting solution, 492 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW precursor had a pH of 11.3 as determined via measurement with a pH-sensitive electrode. From said suspension, the B-MWW precursor was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m² dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 600° C. for 10 h. The calcined material had a molar ratio $B_2O_3:SiO_2$ molar ratio of 0.04:1.

(ii) Deboronation 360 kg of de-ionized water and 12 kg of calcined material were refluxed at 100° C. under stirring at 70 r.p.m. for 20 h. The resulting deboronated zeolitic material was separated from the suspension by filtration and washed with 240 l deionized water at room temperature. After the filtration, the filter cake was dried at a temperature of 120° C. for 48 h.

The dried zeolitic material having an MWW framework structure had a $B_2O_3:SiO_2$ molar ratio of 0.0015:1.

(iii) Incorporation of Sn 675 g deionized water were provided in a glass beaker and 226.1 g piperidine were added under stirring and further stirred for 20 minutes. Separately, in a glovebox 4.35 g tin (IV)-tert-butoxyde were dissolved in 100 g piperidine under nitrogen atmosphere. The mixture was added to the aqueous piperidine suspension and further stirred for 10 minutes. 150 g zeolitic material obtained according to Example 1 (ii) were added to the mixture and stirred for 1 h (200 r.p.m.) at room temperature. The obtained suspension was than filled in an autoclave. The mixture was treated for 120 h at a temperature of 170° C. under stirring (100 r.p.m.).

Afterwards the autoclave was cooled down to room temperature and the resulting zeolitic material was separated from the suspension by filtration at room temperature and washed with deionized water until the washing water had a conductivity of less than 300 microSiemens/cm. After the filtration, the filter cake was dried at a temperature of 120° C. for 16 h.

The dried zeolitic material had a Si content of 43 weight-% and a Sn content of 0.75 weight-%

(iv) Acid Treatment 150 g zeolitic material obtained according to Example 1 (iii) were provided in a round bottom flask and 4.5 kg of a 30 weight-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h.

The dried and cacined zeolitic material hat a Si content of 43 weight-% and a Sn content of 0.75 weight-% and a c parameter as determined via XRD of 26.92 Angstrom. Further, the zeolitic material had a BET surface area, determined according to DIN 66131 of 462 m²/g, a Langmuir surface, determined according to DIN 66131 of 642 m²/g and a total pore area of 76.72 m²/g. Furthermore, the obtained zeolitic material had a X-ray diffraction pattern comprising peaks at 2 theta diffraction angles of (6.6±0.1)°, (7.1±0.1)°, (7.9±0.1)°, (9.6±0.1)°, (12.8±0.1)°, (14.4±0.1)°, (14.7±0.1)°, (15.8±0.1)°, (19.3±0.1)°, (20.1±0.1)°, (21.7±0.1)°, (21.9±0.1)°, (22.6±0.1)°, (22.9±0.1)°, (23.6±0.1)°, (25.1±0.1)°, (26.1±0.1)°, (26.9±0.1)°, (28.6±0.1)°, and (29.1±0.1)°.

Results of Example 2

As Example 1, also Example 2 shows that the inventive process, a combination of a deboronation with the incorporation of Sn, wherein the molar ratio of Sn relative to Si was chosen in such a manner that the finally obtained Sn-MWW had a tin-content lower than 2 weight-%, and subsequent treating with an acidic solution, leads to a tin-containing zeolitic material having an MWW-type framework structure (Sn-MWW) with a high interlayer distance which is given by the lattice parameter c of the framework structure, which parameter c has a value of 26.92 Angstrom.

Comparative Example 1

Preparation of a Conventional Sn-MWW (i) Preparation of B-MWW 470.4 kg de-ionized water were provided in a vessel. Under stirring at 70 rpm (rounds per minute), 162.5 kg boric acid were suspended in the water at room temperature. The suspension was stirred for another 3 h at room temperature. Subsequently, 272.5 kg piperidine were added, and the mixture was stirred for another hour. To the resulting solution, 492 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW precursor had a pH of 11.3 as determined via measurement with a pH-sensitive electrode. From said suspension, the B-MWW precursor was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m²
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 600° C. for 10 h. The calcined material had a molar ratio $B_2O_3$:$SiO_2$ molar ratio of 0.04:1.

(ii) Deboronation 360 kg of de-ionized water and 12 kg of calcined material were refluxed at 100° C. under stirring at 70 r.p.m. for 20 h. The resulting deboronated zeolitic material was separated from the suspension by filtration and washed with 240 l deionized water at room temperature. After the filtration, the filter cake was dried at a temperature of 120° C. for 48 h.

The dried zeolitic material having an MWW framework structure had a $B_2O_3$:$SiO_2$ molar ratio of 0.0015:1.

(iii) Incorporation of Sn 675 g deionized water were provided in a glass beaker and 226.1 g piperidine were added under stirring and further stirred for 20 minutes. Separately, in a glovebox 11.69 g tin(IV)-tert-butoxyde were dissolved in 100 g piperidine under nitrogen atmosphere. The mixture was added to the aqueous piperidine suspension and further stirred for 10 minutes. 150 g zeolitic material obtained according to Example 1 (ii) were added to the mixture and stirred for 1 h (200 r.p.m.) at room temperature. The obtained suspension was than filled in an autoclave. The mixture was treated for 120 h at a temperature of 170° C. under stirring (100 r.p.m.).

Afterwards the autoclave was cooled down to room temperature and the resulting zeolitic material was separated from the suspension by filtration at room temperature and washed with deionized water until the washing water had a conductivity of less than 300 microSiemens/cm. After the filtration, the filter cake was dried at a temperature of 120° C. for 16 h.

The dried zeolitic material hat a Si content of 42 weight-% and a Sn content of 2.1 weight-%.

(iv) Acid-Treatment 150 g zeolitic material obtained according to Comparative Example 2 (iii) were provided in a round bottom flask and 4.5 kg of a 30 weight-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h.

The dried and cacined zeolitic material had a Si content of 42 weight-% and a Sn content of 2.1 weight-% and a c parameter as determined via XRD of 26.64 Angstrom. Further, the zeolitic material had a BET surface area, determined according to DIN 66131 of 456 m²/g, a Langmuir surface, determined according to DIN 66131 of 634 m²/g and a total pore area of 84.48 m²/g. Furthermore, the obtained zeolitic material had a X-ray diffraction pattern comprising peaks at a 2 theta diffraction angle of (7.2±0.1)°, (7.9±0.1)°, (9.9±0.1)°, (12.9±0.1)° (14.4±0.1)°, (14.7±0.1)°, (15.9±0.1)°, (19.2±0.1)°, (20.2±0.1)°, (21.7±0.1)°, (22.0±0.1)°, (23.7±0.1)°, (25.1±0.1)°, (26.1±0.1)°, (27.0±0.1)°, (28.5±0.1)°, (29.2±0.1)°, (31.7±0.1)°, (33.4±0.1)°, (36.5±0.1)°, (37.2±0.1)°, (38.0±0.1)°.

Results of Comparative Example 1

In Comparative Example 1, a tin-containing zeolitic material having an MWW framework structure was prepared, wherein the zeolitic material had a tin-content of 2.1 weight-%. The interlayer distance is given by the lattice parameter c of the framework structure, which has a value of 26.64 Angstrom. Compared with the tin-containing zeolitic material obtained according to the inventive process, the lattice parameter c is significantly lower. As far as the X-ray diffraction pattern is concerned, no peak is present at a 2 theta angle of (6.6±0.1)°, in contrast to the X-ray diffraction pattern of the novel Sn-MWW according to the invention.

Example 3

Use of the Novel Sn-MWW as a Catalyst in the Baeyer-Villiger Oxidation

A glass vessel was charged with 1.5 g cyclohexanone, 45 g acetonitrile and 1.6 g zeolitic material obtained according to Example 1. The mixture was heated to reflux (95° C.). An aqueous solution of 0.5 g $H_2O_2$ (70 weight-%) was added and the reaction mixture was stirred for 4 h. After cooling down to room temperature, the solution was filtrated and the catalyst washed with 50 mL dioxane.

Result of Example 3

In Example 3, a cyclohexanone conversion of 42% was achieved by use of the zeolitic material obtained according to Example 1(iv). Further, the selectivity to the product of the oxidation reaction, i.e. epsilon-caprolactone, was 50%.

Comparative Example 2

Baeyer Villiger Oxidation by Use of the Zeolitic Material Obtained from Comparative Example 1

A glass vessel was charged with 1.5 g cyclohexanone, 45 g acetonitrile and 0.6 g zeolitic material obtained according to Comparative Example 1. The mixture was heated to reflux (95° C.). An aqueous solution of 0.5 g $H_2O_2$ (70 weight-%) was added and the reaction mixture was stirred for 4 h. After cooling down to room temperature, the solution was filtrated and the catalyst washed with 50 mL dioxane.

Result of Comparative Example 2

In Example 3.3, a cyclohexanone conversion of 22% was achieved by use of the zeolitic material obtained according to Example 1(iii). Further, the selectivity to the product of the oxidation reaction, i.e. epsilon-caprolactone, was 37%.

Summary and Comparison of the Results of Example 3 and Comparative Example 2

As shown in table 1 below, using the zeolitic material according to Comparative Example 1, i.e. a conventional tin-containing zeolitic material having MWW framework structure the XRD diffraction pattern of which does not exhibit a peak at a 2 theta diffraction angle of (6.6±0.1), a cyclohexanone conversion of 22% and a selectivity of epsilon-caprolactone relative to the cyclohexanone of 37% was obtained.

When using the novel Sn-MWW material the XRD diffraction pattern of which does exhibit a peak at a 2 theta diffraction angle of (6.6±0.1) and which, therefore, exhibits a higher interlayer distance compared to the conventional material, a significant increase of about 90% in cyclohexanone conversion (42%) as well as a significant increase of about 35% in selectivity (50%) was observed.

TABLE 1

Catalytic activity of the zeolitic materials in the Baeyer-Villiger oxidation

| Used zeolitic material | Cyclohexanone Conversion | Selectivity Caprolactone based on Cyclohexanone |
| --- | --- | --- |
| novel Sn-MWW obtained according to Example 2 | 42% | 50% |
| conventional Sn-MWW obtained according to Comparative Example 1 | 22% | 37% |

Example 4

Preparation of a Novel Sn-MWW (i) As in Example 1 Above
(ii) As in Example 1 Above
(iii) Incorporation of Sn 776.25 g deionized water were provided in a glass beaker and 375 g piperidine were added under stirring. To this suspension 1.45 g of $Sn(OAc)_2$ (Sn(II) acetate) was added and the suspension stirred for another 10 minutes. 172.4 g zeolitic material obtained according to Example 1 (ii) were added to the mixture and stirred for 20 min (200 r.p.m.) at room temperature. The obtained suspension was than filled in an autoclave. The mixture was treated for 48 h at a temperature of 170° C. under stirring (100 r.p.m.).

Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h.

The dried zeolitic material had a Si content of 40 weight-% and a Sn content of 0.42 weight-%.

(iv) Acid Treatment 173.4 g zeolitic material obtained according to Example 4 (iii) were provided in a round bottom flask and 5,202 g of a 30 weight-% $HNO_3$ aqueous solution, having a pH in the range from 0 to 1, were added. The mixture was stirred at a temperature of 100° C. for a period of 20 h (200 r.p.m.) under reflux. The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h.

The dried and cacined zeolitic material hat a Si content of 47 weight-% and a Sn content of 0.46 weight-% and a c parameter as determined via XRD of 26.91 Angstrom. Further, the zeolitic material had a BET surface area, determined according to DIN 66131 of 520 $m^2$/g, and a Langmuir surface, determined according to DIN 66131 of 713 $m^2$/g. Furthermore, the obtained zeolitic material had a X-ray diffraction pattern comprising peaks at 2 theta diffraction angles of (6.6±0.1)°, (7.1±0.1)°, (7.9±0.1)°, (9.6±0.1)°, (12.8±0.1)°, (14.4±0.1)°, (14.7±0.1)°, (15.8±0.1)°, (19.3±0.1)°, (20.1±0.1)°, (21.7±0.1)°, (21.9±0.1)°, (22.6±0.1)°, (22.9±0.1)°, (23.6±0.1)°, (25.1±0.1)°, (26.1±0.1)°, (26.9±0.1)°, (28.6±0.1)°, and (29.1±0.1)°.

Results of Example 4

As Examples 1 and 2, also Example 4 shows that the inventive process, a combination of a deboronation with the incorporation of Sn, wherein the molar ratio of Sn relative to Si was chosen in such a manner that the finally obtained Sn-MWW had a tin-content lower than 2 weight-%, and subsequent treating with an acidic solution, leads to a tin-containing zeolitic material having an MWW-type framework structure (Sn-MWW) with a high interlayer distance which is given by the lattice parameter c of the framework structure, which parameter c has a value of 26.91 Angstrom. Test of the Material of Example 4 in the Baeyer-Villiger Oxidation of Cyclohexanone to Epsilon-Caprolactone in 1,2-Dichloroethane as Solvent A 100 ml glass flask vessel was charged with 1.5 g cyclohexanone, 1.2 g zeolitic material obtained according to Reference Example 2, having a Sn content of 0.46 weight-% and 45 g dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-n-butyl ether as internal standard. Epsilon-caprolactone was obtained, wherein a selectivity to epsilon-caprolactone based on cyclohexanone of 54% was achieved.

Example 5

Preparation of a Novel Sn-MWW, and Preparation of a Molding (i) Preparation of B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50 to 60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:

drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m²
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 650° C. in a rotary oven in contra current flow (0.8-1 kg/h). The calcined material had a B content of 1.4 weight-%, a Si content of 43 wt. %, and TOC of less than 0.1 wt. %. The material had a BET specific surface area, measured according to DIN 66131, of 468 m²/g.

(ii) Deboronation 1,590 kg of de-ionized water and 106 kg of the calcined material obtained from (i) were refluxed at 100° C. under stirring at 70 r.p.m. for 10 h. The resulting deboronated zeolitic material was separated from the suspension by filtration and washed 4 times with 150 l deionized water at room temperature. After the filtration, the filter cake was dried at a temperature of 120° C. for 16 h.

The dried zeolitic material having an MWW framework structure had a B content of 0.04 weight-%, a Si content of 42 weight-%, and a BET specific surface area, measured according to DIN 66131, of 462 m²/g.

(iii) Incorporation of Sn 776.25 g deionized water were provided in a glass beaker and 375 g piperidine were added under stirring. To this suspension 2.5 g of Sn(IV)butoxyde predissolved in 25 g piperidine were added and the suspension was stirred for another 10 minutes. 172.4 g deboronated zeolitic material obtained according to (ii) above were added to the mixture and stirred for 60 min (200 r.p.m.) at room temperature. The obtained suspension was than filled in an autoclave. The mixture was treated for 120 h at a temperature of 170° C. under stirring (100 r.p.m.). Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h.

The dried zeolitic material had a Si content of 40 weight-% and a Sn content of 0.42 weight-%.

(iv) Acid Treatment 174 g tin containing zeolitic material obtained from (iii) above were provided in a round bottom flask and 5,220 kg of a 30 weight-% HNO₃ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2 K/min) and subsequent heating at 550° C. for 10 h.

The dried and cacined zeolitic material hat a Si content of 49 weight-% and a Sn content of 0.46 weight-% and a c parameter as determined via XRD of 27.1 Angstrom. Further, the zeolitic material had a BET surface area, determined according to DIN 66131, of 521 m²/g, a Langmuir surface, determined according to DIN 66131 of 695 m²/g.

(v) Preparation of a Molding 140 g of the zeolitic calcined zeolitic material obtained from (iv) and 8.4 g Walocel were kneaded for 5 min in an edge mill. During kneading, 82.6 g Ludox® AS-40 were added continuously. After 10 min, the addition of 150 ml de-ionized water was started. After another 30 min, die kneading mass was adjusted by addition of 30 ml de-ionized water. After a total kneading time of 50 min, the mass is extrudable, and the mass was extruded at a pressure of from 100 to 150 bar during 1 min. The obtained strands were dried at 120° C. for 8 h in an oven and calcined at 500° C. for 5 h. 137.2 g of white strands were obtained, having a diameter of 1.7 mm.

The dried and caclined material in the form of said strands had a Si content of 46 weight-%, a Sn content of 0.41 weight-% and TOC of 0.01 weight-%. Further, the strands had a BET surface area, determined according to DIN 66131, of 412 m²/g, and a pore volume determined by Hg porosimetry of 0.91 ml/g.

Test of the Shaped Material of Example 5 in the Baeyer-Villiger Oxidation of Cyclohexa-None to Epsilon-Caprolactone in Acetonitrile as Solvent A tubular reactor (length: 1.4 m, internal diameter: 7 mm) equipped with a jacket for thermostatization was charged with 15 g of the catalyst obtained from (v) above in the form of strands with a diameter of 1.7 mm. The remaining reactor volume was filled with inert material (steatite spheres, 2 mm in diameter, to a height of about 5 cm at the lower end of the reactor and the remainder at the top end of the reactor). The reactor was thermostatized by flowing a heat transfer medium, a mixture of water and ethylene glycol, through the jacket. The heat transfer medium was fed at the lower end of the jacket so that it flew in cocurrent mode to the reactor contents. The temperature of the heat transfer medium at the entrance of the jacket is defined as the reaction temperature. The flow rate of the heat transfer medium was adjusted so that the difference between entrance and exit temperature was at most 1 K. Pressure in the reactor was con-trolled by a suitable pressure control valve and maintained constant at 20 bar (abs).

The reactor feed stream was metered by using a metering pump. The stream consisted of a mixture of acetonitrile (93.6 weight-%), cyclohexanone (2.5 weight-%), an aqueous hydrogen peroxide solution with a concentration of 40 weight-% (3.9 weight-%) (flow rate: 40 g/h). Under the conditions used the feed was liquid and only one liquid phase was present.

The experiment was performed in a continuous manner. At the start of the run (t=0 is defined at which the metering pump was started) the reaction temperature was set to 90° C. After a certain period of time (usually within 4 hours on stream) a stationary state was reached. The reactor effluent after the pressure control valve was collected, weighed and analyzed by GC using di-n-butylether as internal standard.

Epsilon-caprolactone was obtained, wherein a selectivity to epsilon-caprolactone based on cyclohexanone of 40% was achieved.

SHORT DESCRIPTION OF THE FIGURES

FIG. 1 shows the X-ray diffraction pattern (copper K alpha radiation) of the inventive zeolitic material obtained according to Example 1, which has a tin-content of 0.78 weight-%, calculated as element and based on the weight of the Sn-MWW and a c parameter of 27.069 Angstrom. On the x axis, the degree values (2 Theta) are shown, on the y axis, the intensity (Lin (Counts)). Tick mark labels on the x axis are, from left to right, 2, 10, 20, 30, 40, 50, 60, 70.

Figure 2:
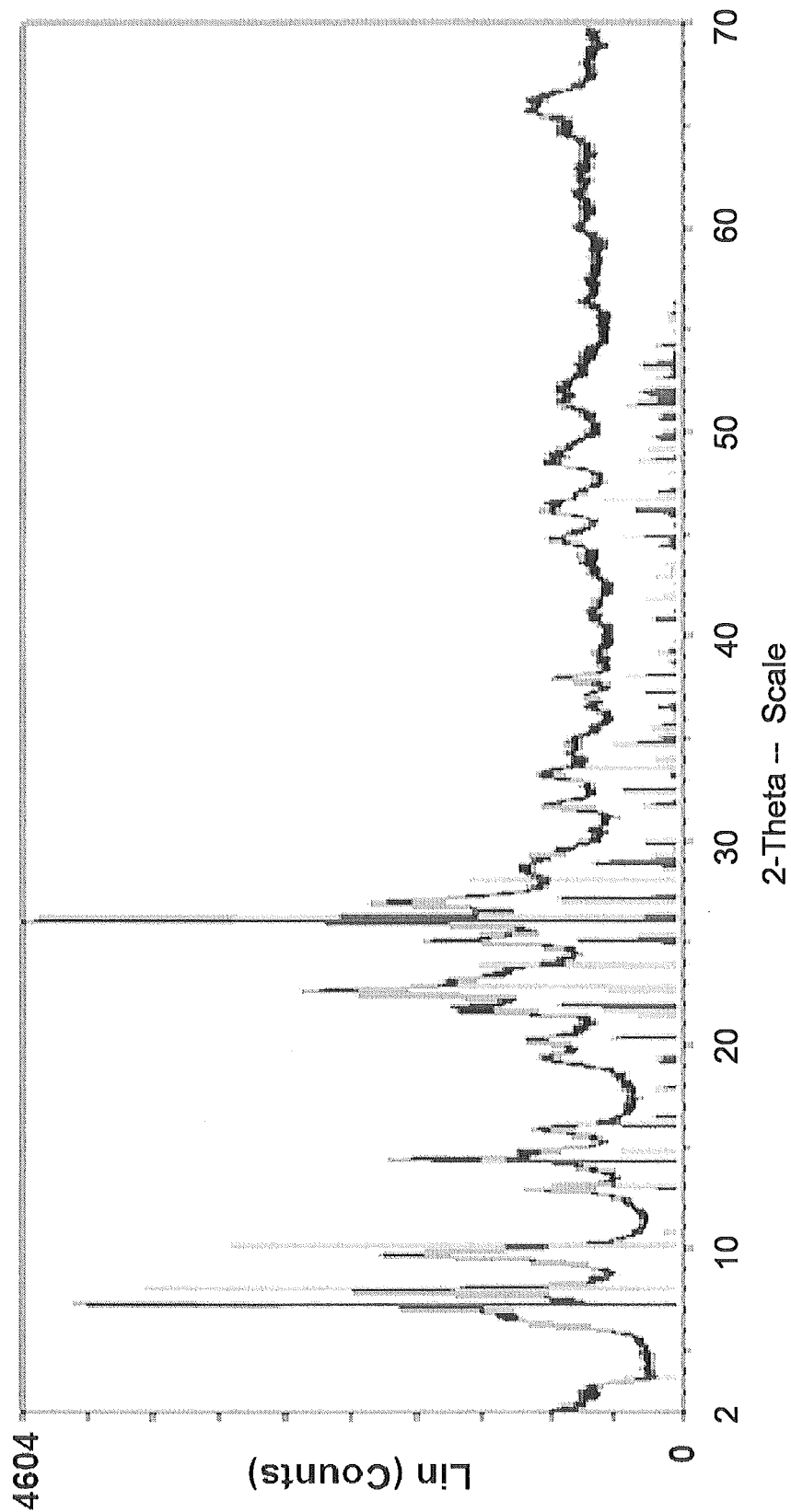

FIG. 2 shows the X-ray diffraction pattern (copper K alpha radiation) of the inventive zeolitic material obtained according to Example 2, which has a tin-content of 0.75 weight-%, calculated as element and based on the weight of the Sn-MWW and a c parameter of 26.92 Angstrom. On the x axis, the degree values (2 Theta) are shown, on the y axis, the intensity (Lin (Counts)). Tick mark labels on the x axis are, from left to right, 2, 10, 20, 30, 40, 50, 60, 70.

Figure 3:
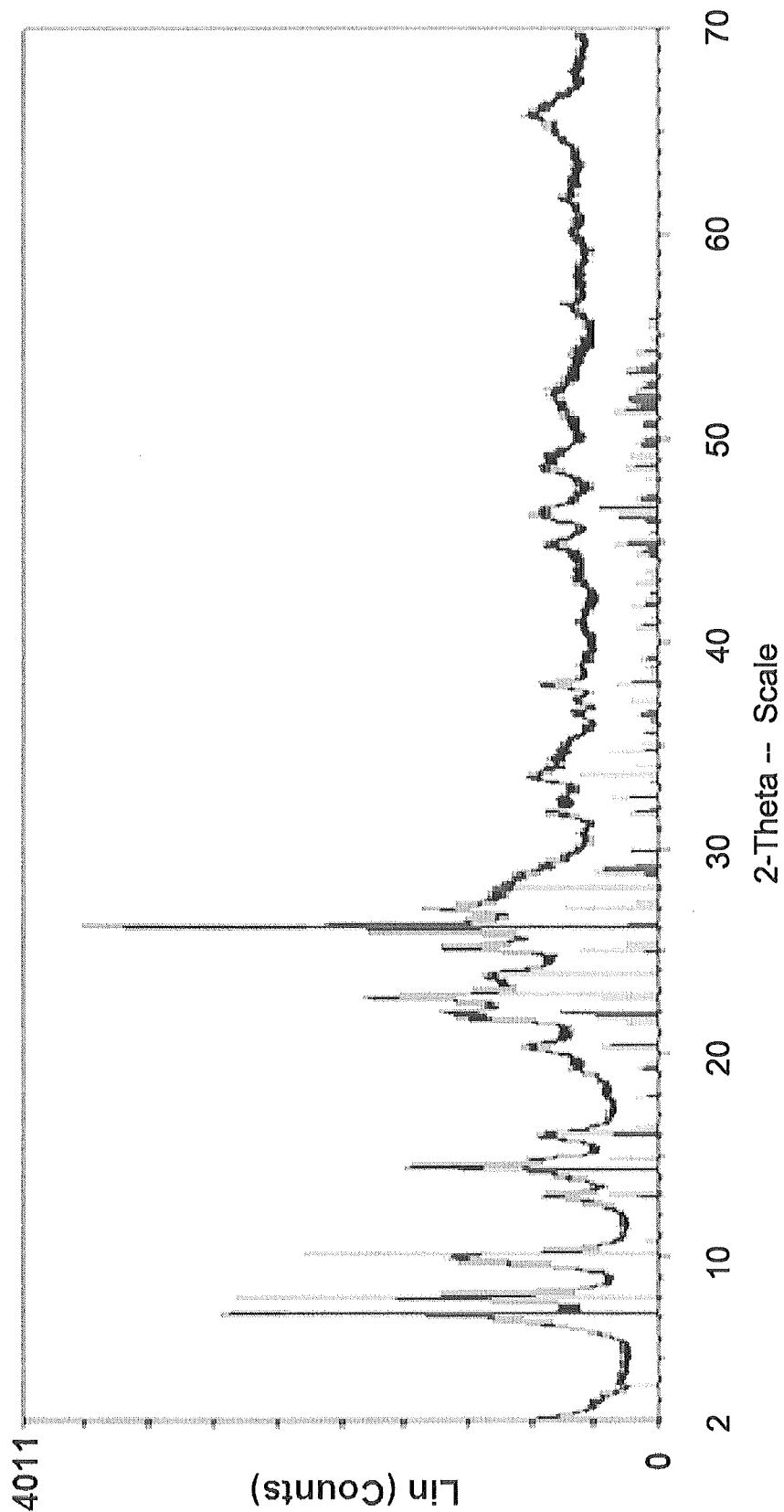

FIG. 3 shows the X-ray diffraction pattern (copper K alpha radiation) of the zeolitic material obtained according to Comparative Example 1, which has a tin-content of 2.1 weight %, calculated as element and based on the weight of the Sn-MWW, and a c parameter of 26.64 Angstrom. On the x axis, the degree values (2 Theta) are shown, on the y axis, the intensity (Lin (Counts)). Tick mark labels on the x axis are, from left to right, 2, 10, 20, 30, 40, 50, 60, 70.

Figure 4:
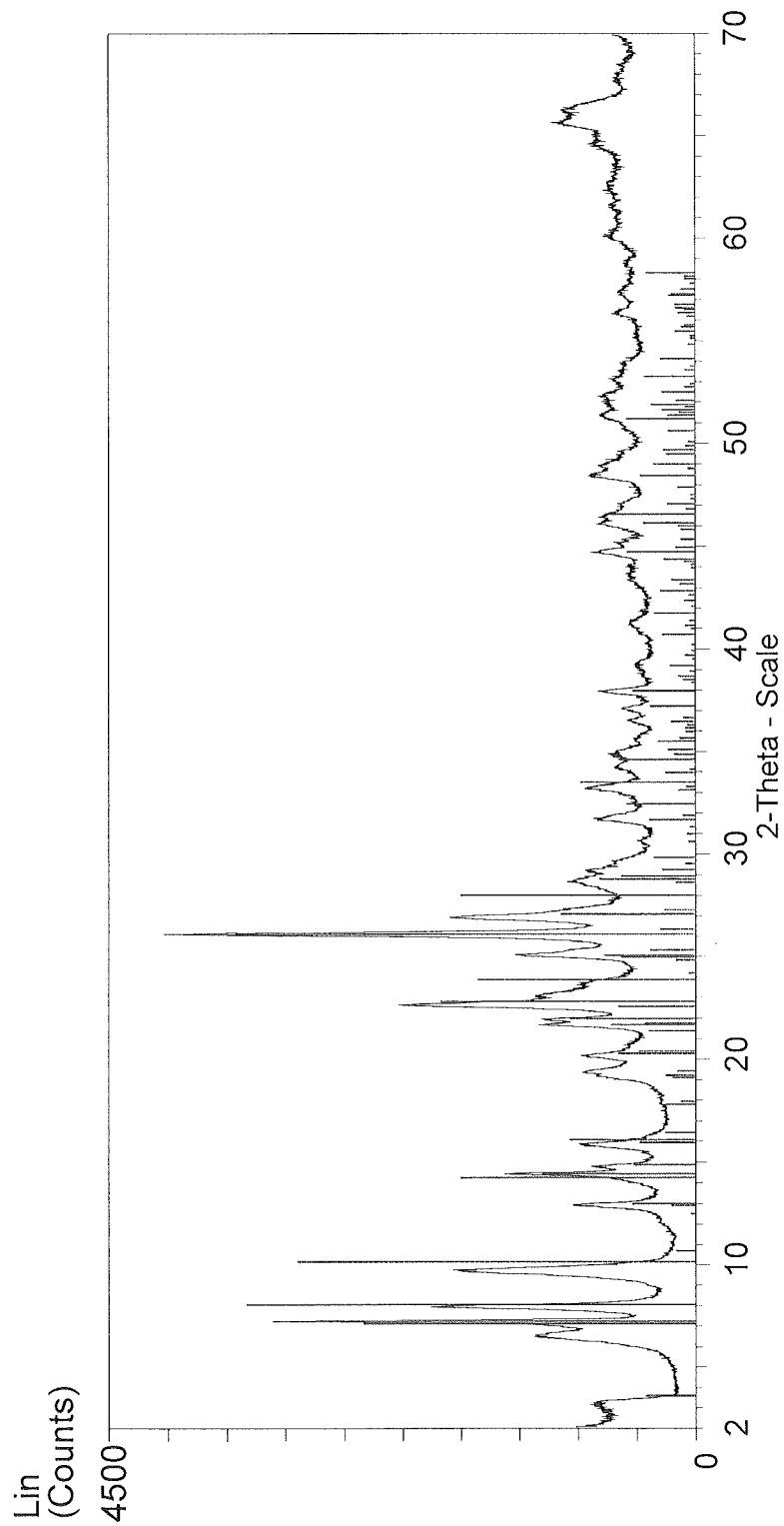

FIG. 4 shows the X-ray diffraction pattern (copper K alpha radiation) of the inventive zeolitic material obtained according to Example 4, which has a tin-content of 0.47 weight-%, calculated as element and based on the weight of the Sn-MWW and a c parameter of 26.92 Angstrom. On the x axis, the degree values (2 Theta) are shown, on the y axis, the intensity (Lin (Counts)). Tick mark labels on the x axis are, from left to right, 2, 10, 20, 30, 40, 50, 60, 70.

CITED LITERATURE

U.S. Pat. No. 5,968,473
U.S. Pat. No. 6,306,364
U.S. Pat. No. 7,326,401 B2
WO03/074422 A1
Microporous and Mesoporous Materials 165 (2013), pages 210-218
Nature 412 (2001), pages 423-425
Journal of Catalysis 234 (2005), pages 96-100

The invention claimed is:

1. A process for preparing a tin-containing zeolitic material having an MWW-type framework structure (Sn-MWW) comprising
   (i) providing a boron-containing zeolitic material having an MWW framework structure comprising $SiO_2$ and $B_2O_3$ (B-MWW);
   (ii) deboronating the B-MWW by treating the B-MWW provided in (i) with a liquid solvent system having a pH in the range of from 5.5 to 8;
   (iii) incorporating Sn into deboronated B-MWW obtained from (ii) by a process comprising
      (iii.1) preparing an aqueous synthesis mixture containing the deboronated B-MWW obtained from (ii), an MWW template compound, and a tin source, wherein in the synthesis mixture, the molar ratio of Sn, calculated as $SnO_2$, relative to Si, calculated as $SiO_2$ and contained in the deboronated B-MWW, is at most 0.015:1;
      (iii.2) hydrothermally synthesizing a tin-containing zeolitic material having an MWW-type framework structure from the synthesis mixture obtained from (iii.1) thereby obtaining a tin-containing zeolitic material having an MWW-type framework structure in its mother liquor;
      (iii.3) separating the tin-containing zeolitic material having an MWW-type framework structure obtained from (iii.2) from its mother liquor;
   (iv) treating the tin-containing zeolitic material having an MWW-type framework structure obtained from (iii) with an aqueous solution having a pH of at most 5 thereby obtaining the Sn-MWW having an Sn content of at most 2 weight-%, calculated as element and based on the weight of the Sn-MWW, and optionally separating the Sn-MWW from the aqueous solution.

2. The process of claim 1, wherein in (i), the B-MWW is provided by a process comprising
   (a) hydrothermally synthesizing a B-MWW precursor from an aqueous synthesis mixture containing a silicon source, a boron source, and an MWW template compound, to obtain the B-MWW precursor in its mother liquor;
   (b) separating the B-MWW precursor from its mother liquor, comprising drying the B-MWW precursor,
   wherein in the synthesis mixture in (a),
   the molar ratio of B, calculated as $B_2O_3$ and contained in the boron source, relative to Si, calculated as $SiO_2$ and contained in the Si source, is in the range of from 0.4:1 to 0.6:1;
   the molar ratio of the MWW template compound, relative to Si, calculated as $SiO_2$ and contained in the Si source, is in the range of from 0.8:1 to 1.7:1; and the molar ratio of $H_2O$ relative to Si, calculated as $SiO_2$ and contained in the Si source, is in the range of from 12:1 to 20:1.

3. The process of claim 2, wherein (b) further comprises calcination of the separated B-MWW precursor, wherein the calcination is carried out at a temperature in the range of from 400 to 800° C.

4. The process of claim 1, wherein in (i), at least 99 weight-% of the framework structure of the B-MWW consists of $B_2O_3$ and $SiO_2$ and the molar ratio $B_2O_3:SiO_2$ of the B-MWW is at least 0.03:1.

5. The process of claim 1, wherein in (ii), the liquid solvent system is selected from the group consisting of water, methanol, ethanol, propanol, ethane-1,2-diol, propane-1,2-diol, propane-1,3-diol, propane-1,2,3-triol, and mixtures of two or more thereof, wherein the liquid solvent system does not contain an inorganic or organic acid, or a salt thereof.

6. The process of claim 1, wherein in (ii), the weight ratio of the liquid solvent system relative to B-MWW is in the range of from 40:1 to 5:1, the treating is carried out at a temperature in the range of from 50 to 125° C., and for a period in the range of from 6 to 20 h.

7. The process of claim 1, wherein in (ii), the treating is carried out in a closed system under autogenous pressure or in an open system under reflux.

8. The process of claim 1, wherein (ii) further comprises drying the deboronated B-MWW at a temperature in the range of from 100 to 180° C.

9. The process of claim 1, wherein (ii) further comprises calcination of the separated deboronated B-MWW, wherein the calcination is carried out at a temperature in the range of from 400 to 800° C.

10. The process of claim 1, wherein the deboronated B-MWW has a molar ratio $B_2O_3:SiO_2$ of at most 0.01:1.

11. The process of claim 1, wherein the tin source is selected from the group consisting of $SnCl_4$, Sn(IV)-acetate, Sn(IV)-tert-butoxide, $SnBr_4$, $SnCl_4$, $SnF_4$, Sn(IV)-bisacetylacetonate dichloride, Sn(IV)-bisacetylacetonate dibromide, Sn(II)-acetate, Sn(II)acetylacetonate, Sn(II)-citrate, $SnCl_2$, $SnF_2$, $SnI_2$, $SnSO_4$, and a mixture of two or more thereof.

12. The process of claim 1, wherein in the aqueous synthesis mixture in (iii.1), the molar ratio of Sn, calculated as $SnO_2$, relative to Si, calculated as $SiO_2$ and contained in the deboronated B-MWW, is in the range of from 0.001:1 to 0.015:1, the molar ratio of the MWW template compound relative to Si, calculated as $SiO_2$ and contained in the deboronated B-MWW, is in the range of from 1.0:1 to 2.0:1, and the molar ratio of $H_2O$ relative to Si, calculated as $SiO_2$ and contained in the deboronated B-MWW, is in the range of from 10:1 to 20:1.

13. The process of claim 1, wherein the hydrothermal synthesizing according to (iii.2) is carried out at a temperature in the range of from 80 to 250° C., for a period in the range of from 20 to 200 h.

14. The process of claim 1, wherein (iii.3) further comprises drying the tin-containing zeolitic material having an MWW-type framework structure, wherein the drying is carried out at a temperature in the range of from 100 to 180° C.

15. The process of claim 1, wherein in (iii.3) and before (iv), the separated tin-containing zeolitic material having an MWW-type framework structure is not subjected to calcination.

16. The process of claim 1, wherein in (iv), the aqueous solution comprises an organic acid selected from the group consisting of oxalic acid, acetic acid, citric acid, methane sulfonic acid, and a mixture of two or more thereof, and/or an inorganic acid selected from the group consisting of phosphoric acid, sulphuric acid, hydrochloric acid, nitric acid, and a mixture of two or more thereof, and wherein the aqueous solution has a pH in the range of from 0 to 5.

17. The process of claim 1, wherein in (iv), the tin-containing zeolitic material having an MWW-type framework structure is treated with the aqueous solution at a temperature in the range of from 50 to 175° C., for a period in the range of from 1 to 40 h.

18. The process of claim 1, wherein in (iv), the weight ratio of the aqueous solution relative to the tin-containing zeolitic material having an MWW-type framework structure is in the range of from 10:1 to 50:1.

19. The process of claim 1, wherein in (iv), the treating is carried out in a closed system under autogenous pressure or in an open system under reflux.

20. The process of claim 1, wherein the tin content of the Sn-MWW obtained from (iv), calculated as element and based on the weight of the Sn-MWW, is in the range of from 0.1 to 1.9 weight-%.

21. The process of claim 1, wherein (iv) comprises drying the Sn-MWW, wherein the drying is carried out at a temperature in the range of from 100 to 180° C., and wherein (iv) comprises calcination of the separated and dried Sn-MWW, wherein the calcination is carried out at a temperature in the range of from 400 to 800° C., for a period in the range of from 1 to 20 h.

22. The process of claim 1, further comprising
(v) preparing a moldable mixture comprising the Sn-MWW obtained from (iv), the moldable mixture optionally comprising a binder or a binder precursor;
(vi) subjecting the mixture obtained from (v) to shaping, to obtain a molding containing the Sn-MWW; and
(vii) optionally drying and/or calcining the molding obtained in (v).

23. A zeolitic material obtained by the process according to claim 1.

24. A tin containing zeolitic material having an MWW-type framework structure (Sn-MWW), having a tin content of at most 2 weight-%, calculated as element and based on the weight of the Sn-MWW, and having an X-ray diffraction pattern comprising a peak at a 2 theta diffraction angle of (6.6±0.1)°.

25. The zeolitic material of claim 24, wherein the zeolitic material has a tin content in the range of from 0.4 to 1.0 weight-%, calculated as element and based on the weight of the Sn-MWW.

26. The zeolitic material of claim 24, having an X-ray diffraction pattern comprising a peak at a 2 theta diffraction angle of (6.6±0.1)°, a peak at a 2 theta diffraction angle of (7.1±0.1)°, and a peak at a 2 theta diffraction angle of (7.9±0.1)°.

27. The zeolitic material of claim 24, having an X-ray diffraction pattern comprising peaks at a 2 theta diffraction angle of (6.6±0.1)°, (7.1±0.1)°, (7.9±0.1)°, (9.6±0.1)°, (12.8±0.1)°, (14.4±0.1)°, (14.7±0.1)°, (15.8±0.1)°, (19.3±0.1)°, (20.1±0.1)°, (21.7±0.1)°, (21.9±0.1)°, (22.6±0.1)°, (22.9±0.1)°, (23.6±0.1)°, (25.1±0.1)°, (26.1±0.1)°, (26.9±0.1)°, (28.6±0.1)°, and (29.1±0.1)°.

28. The zeolitic material of claim 24, wherein the c parameter, as determined via XRD, is (27.1±0.2) Angstrom.

29. The zeolitic material of claim 24, wherein the MWW-type framework structure of the Sn-MWW comprises $SiO_2$ and $B_2O_3$ and the molar ratio $B_2O_3:SiO_2$ is at most 0.01:1, wherein at least 99 weight-% of the MWW-type framework structure of the Sn-MWW consists essentially of $SiO_2$ and $B_2O_3$.

30. The zeolitic material of claim 24, obtained by a process comprising
   (i) providing a boron-containing zeolitic material having an MWW framework structure comprising $SiO_2$ and $B_4O_3$ (B-MWW);
   (ii) deboronating the B-MWW by treating the B-MWW provided in (i) with a liquid solvent system having a pH in the range of from 5.5 to 8;
   (iii) incorporating Sn into the deboronated B-MWW obtained from (ii) by a process comprising
      (iii.1) preparing an aqueous synthesis mixture containing the deboronated B-MWW obtained from (ii), an MWW template compound, and a tin source, wherein in the synthesis mixture, the molar ratio of Sn, calculated as $SnO_2$, relative to Si, calculated as $SiO_2$ and contained in the deboronated B-MWW, is at most 0.015:1;
      (iii.2) hydrothermally synthesizing a tin-containing zeolitic material having an MWW-type framework structure from the synthesis mixture obtained from (iii.1) thereby obtaining a tin-containing zeolitic material having an MWW-type framework structure in its mother liquor;
      (iii.3) separating the tin-containing zeolitic material having an MWW-type framework structure obtained from (iii.2) from its mother liquor;
   (iv) treating the tin-containing zeolitic material having an MWW-type framework structure obtained from (iii) with an aqueous solution having a pH of at most 5 thereby obtaining the Sn-MWW having an Sn content of at most 2 weight-%, calculated as element and based on the weight of the Sn-MWW, and optionally separating the Sn-MWW from the aqueous solution.

31. The zeolitic material of claim 24, wherein the zeolitic material is in the form of a spray-powder.

32. An oxidation process comprising reacting a compound with an oxidizing agent in the presence of the zeolitic material according to claim 24.

33. The process of claim 32, wherein the oxidation process is a Baeyer-Villiger oxidation, wherein the compound is an organic carbonyl compound and wherein the oxidizing agent is a peroxyacid or a peroxide.

34. A molding comprising the zeolitic material of claim 24 and a binder.

* * * * *